US012675861B2

(12) United States Patent
Kunz et al.

(10) Patent No.: US 12,675,861 B2
(45) Date of Patent: Jul. 7, 2026

(54) SYSTEMS AND METHODS FOR PROCESSING ELECTRONIC IMAGES TO IDENTIFY TRANSPLANT DONOR-RECIPIENT MATCHES

(71) Applicant: PAIGE.AI, Inc., New York, NY (US)

(72) Inventors: Jeremy Daniel Kunz, New York, NY (US); Christopher Kanan, Pittsford, NY (US)

(73) Assignee: Paige.AI, Inc., New York, NY (US)

( * ) Notice: Subject to any disclaimer, the term of this patent is extended or adjusted under 35 U.S.C. 154(b) by 463 days.

(21) Appl. No.: 18/330,745

(22) Filed: Jun. 7, 2023

(65) Prior Publication Data

US 2023/0401685 A1 Dec. 14, 2023

Related U.S. Application Data

(60) Provisional application No. 63/366,015, filed on Jun. 8, 2022.

(51) Int. Cl.
| | |
|---|---|
| *G06T 7/00* | (2017.01) |
| *A61B 17/00* | (2006.01) |

(Continued)

(52) U.S. Cl.
CPC ........... *G06T 7/0002* (2013.01); *G16H 10/60* (2018.01); *G16H 50/20* (2018.01); *G16H 50/70* (2018.01);

(Continued)

(58) Field of Classification Search
CPC ......... G06T 7/0002; G06T 2207/20081; G06T 2207/30056; G06T 7/001; G06T 7/0012;

(Continued)

(56) References Cited

U.S. PATENT DOCUMENTS

| | | | |
|---|---|---|---|
| 10,448,956 B2 | 10/2019 | Gordon et al. | |
| 11,574,140 B2 | 2/2023 | Sue et al. | |

(Continued)

OTHER PUBLICATIONS

Olekhnovich EI, Ivanov AB, Ulyantsev VI, Ilina EN. 2021. Separation of Donor and Recipient Microbial Diversity Allows Determination of Taxonomic and Functional [ . . . ]. mSystems 6:10. 1128/msystems.00811-21. https://doi.org/10.1128/msyste (Year: 2021).*

(Continued)

*Primary Examiner* — Utpal D Shah
*Assistant Examiner* — Jack Peter Kraynak
(74) *Attorney, Agent, or Firm* — Bookoff McAndrews, PLLC

(57) ABSTRACT

Systems and methods are described herein for processing electronic medical images to predict one or more donor recipients for a patient. For example, a digital medical image of the patient may be received, wherein the patient is in need of a transplant. A trained machine learning system may be determined. The digital medical image may be provided into the trained machine learning system, the trained machine learning system determining a patient embedding. Using the patient embedding, a subset of donor recipients may be determined. Based on the subset of donor recipients a recommendation of optimal donors may be determined.

17 Claims, 14 Drawing Sheets

450

452 — RECEIVE THE TRAINED MACHINE LEARNING SYSTEM

454 — RECEIVE AT LEAST A DIGITAL MEDICAL IMAGE (E.G., A WHOLE SLIDE IMAGE AND/OR RADIOLOGY IMAGE) OF A PATIENT IN NEED OF A TRANSPLANT OF THE GIVEN TYPE FROM A DONOR

456 — PROVIDE AT LEAST THE DIGITAL MEDICAL IMAGE AS INPUT TO THE TRAINED MACHINE LEARNING MODEL

458 — RECEIVE THE RECOMMENDATION OF OPTIMAL DONOR(S) AS OUTPUT OF THE TRAINED MACHINE LEARNING MODEL

460 — SAVE THE RECOMMENDATION TO A DIGITAL STORAGE (E.G., TO A MEDICAL RECORD ASSOCIATED WITH THE PATIENT).

(51) Int. Cl.
    *G16H 10/60*         (2018.01)
    *G16H 50/20*         (2018.01)
    *G16H 50/70*         (2018.01)

(52) U.S. Cl.
    CPC .............. *A61B 2017/00969* (2013.01); *G06T 2207/20081* (2013.01); *G06T 2207/30056* (2013.01)

(58) Field of Classification Search
    CPC ........... G06T 7/0014; G06T 7/10; G06T 7/11; G16H 10/60; G16H 50/70; G16H 50/20; A61B 2017/00969; G06N 3/006
    See application file for complete search history.

(56)          References Cited

U.S. PATENT DOCUMENTS

| | | | | |
|---|---|---|---|---|
| 11,961,224 | B2 * | 4/2024 | Labiche | ................. G06T 7/0012 |
| 2012/0123792 | A1 * | 5/2012 | Klein | ...................... G16H 10/60 |
| | | | | 705/2 |
| 2016/0328515 | A1 * | 11/2016 | Campagne | ............. G16B 30/20 |
| 2017/0143427 | A1 * | 5/2017 | Grady | ................... G06T 7/0012 |
| 2020/0118684 | A1 * | 4/2020 | Mark | ...................... G16H 50/20 |
| 2021/0073986 | A1 | 3/2021 | Kapur et al. | |
| 2023/0132247 | A1 * | 4/2023 | Hopkins | ............... G06F 40/279 |
| | | | | 705/2 |
| 2025/0069722 | A1 * | 2/2025 | Sajadi | .................... G06N 3/048 |

OTHER PUBLICATIONS

Tran, J., Sharma, D., Gotlieb, N. et al. Application of machine learning in liver transplantation: a review. Hepatol Int 16, 495-508 (2022). https://doi.org/10.1007/s12072-021-10291-7Asd (Year: 2022).*

Bibbò, S., Settanni, C. R., Porcari, S., Bocchino, E., Ianiro, G., Cammarota, G., & Gasbarrini, A. (2020). Fecal Microbiota Transplantation: Screening and Selection to Choose the Optimal Donor. Journal of clinical medicine, 9(6), 1757. https://doi.org/10.3390/jcm9061757 (Year: 2020).*

Bibbò S, Settanni CR, Porcari S, Bocchino E, Ianiro G, Cammarota G, Gasbarrini A. Fecal Microbiota Transplantation: Screening and Selection to Choose the Optimal Donor. J Clin Med. Jun. 5, 2020;9(6): 1757. doi: 10.3390/jcm9061757. PMID: 32517023; PMCID: PMC7356099.

Deborah Nejman, et al.,The human tumor microbiome is composed of tumor type-specific intracellular bacteria. Science 368, 973-980 (2020). DOI:10.1126/science.aay9189.

Nakashima H, Kawahira H, Kawachi H, Sakaki N. Artificial intelligence diagnosis of Helicobacter pylori infection using blue laser imaging-bright and linked color imaging: a single-center prospective study. Ann Gastroenterol. Jul.-Aug. 2018;31(4):462-468. doi: 10.20524/aog.2018.0269. Epub May 3, 2018. PMID: 29991891; PMCID: PMC6033753.

Fecal transplant (2022) Fecal Transplant | Johns Hopkins Medicine. Available at: https://www.hopkinsmedicine.org/health/treatment-tests-and-therapies/fecal-transplant (Accessed: Jun. 6, 2023).

Huse SM, Young VB, Morrison HG, Antonopoulos DA, Kwon J, Dalal S, Arrieta R, Hubert NA, Shen L, Vineis JH, Koval JC, Sogin ML, Chang EB, Raffals LE. Comparison of brush and biopsy sampling methods of the ileal pouch for assessment of mucosa-associated microbiota of human subjects. Microbiome. Feb. 14, 2014;2(1):5. doi: 10.1186/2049-2618-2-5. PMID: 24529162; PMCID: PMC3931571.

Wilson, B.C. et al. (2019) The super-donor phenomenon in fecal microbiota transplantation. Available at: https://www.frontiersin.org/articles/10.3389/fcimb.2019.00002/full (Accessed: Jun. 6, 2023).

Cho, Janice M., et al. (2019) Fecal microbiota transplant via colonoscopy may be preferred due to intraprocedure findings. Intestinal Research, 2019; 17(3): 434-437. Published online May 31, 2019, DOI:https://doi.org/10.5217/ir.2019.00056.

Connor, Katie L., et al. "The future role of machine learning in clinical transplantation." Transplantation 105.4 (Sep. 2020): 723-735.

Park, Rohee, et al. "Accuracy and efficiency of right-lobe graft weight estimation using deep-learning-assisted CT volumetry for living-donor liver transplantation." Diagnostics 12.3 (Feb. 2022): 590.

Tran, Jason, et al. "Application of machine learning in liver transplantation: a review." Hepatology International 16.3 (Jan. 2022): 495-508.

\* cited by examiner

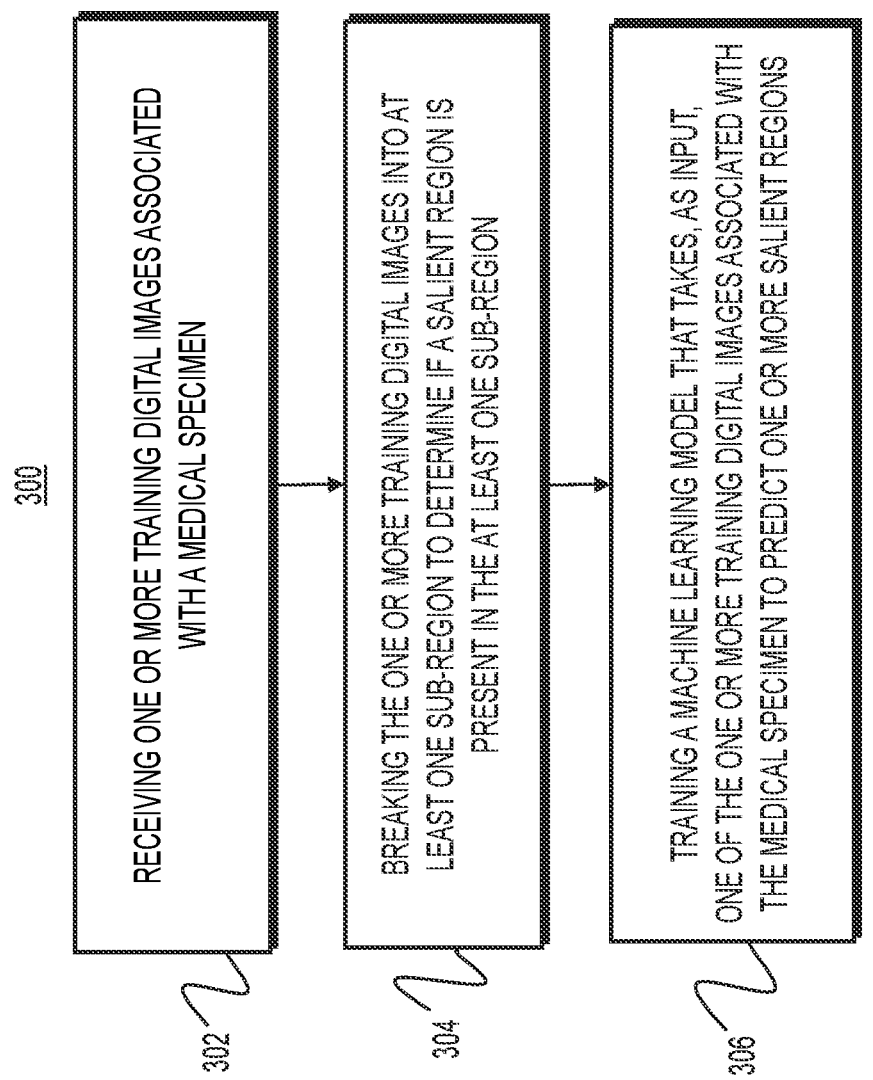

300

RECEIVING ONE OR MORE TRAINING DIGITAL IMAGES ASSOCIATED WITH A MEDICAL SPECIMEN

302

BREAKING THE ONE OR MORE TRAINING DIGITAL IMAGES INTO AT LEAST ONE SUB-REGION TO DETERMINE IF A SALIENT REGION IS PRESENT IN THE AT LEAST ONE SUB-REGION

304

TRAINING A MACHINE LEARNING MODEL THAT TAKES, AS INPUT, ONE OF THE ONE OR MORE TRAINING DIGITAL IMAGES ASSOCIATED WITH THE MEDICAL SPECIMEN TO PREDICT ONE OR MORE SALIENT REGIONS

352 — RECEIVING ONE OR MORE DIGITAL MEDICAL IMAGES ASSOCIATED WITH A TARGET PATHOLOGY SPECIMEN

354 — APPLYING A TRAINED MACHINE LEARNING MODEL TO IDENTIFY AT LEAST ONE SALIENT REGION TO BE ANALYZED IN THE ONE OR MORE DIGITAL MEDICAL IMAGES

356 — OUTPUTTING ONE OR MORE SALIENT REGION TO AN ELECTRONIC STORAGE DEVICE

400

402 — RECEIVE A PLURALITY OF DONOR-RECIPIENT PAIR PROFILES ASSOCIATED WITH PREVIOUSLY PERFORMED TRANSPLANTS OF A GIVEN TYPE

404 — GENERATE AND TRAIN A MACHINE LEARNING SYSTEM USING THE TRAINING DATA

406 — SAVE THE TRAINED MACHINE LEARNING SYSTEM IN DIGITAL

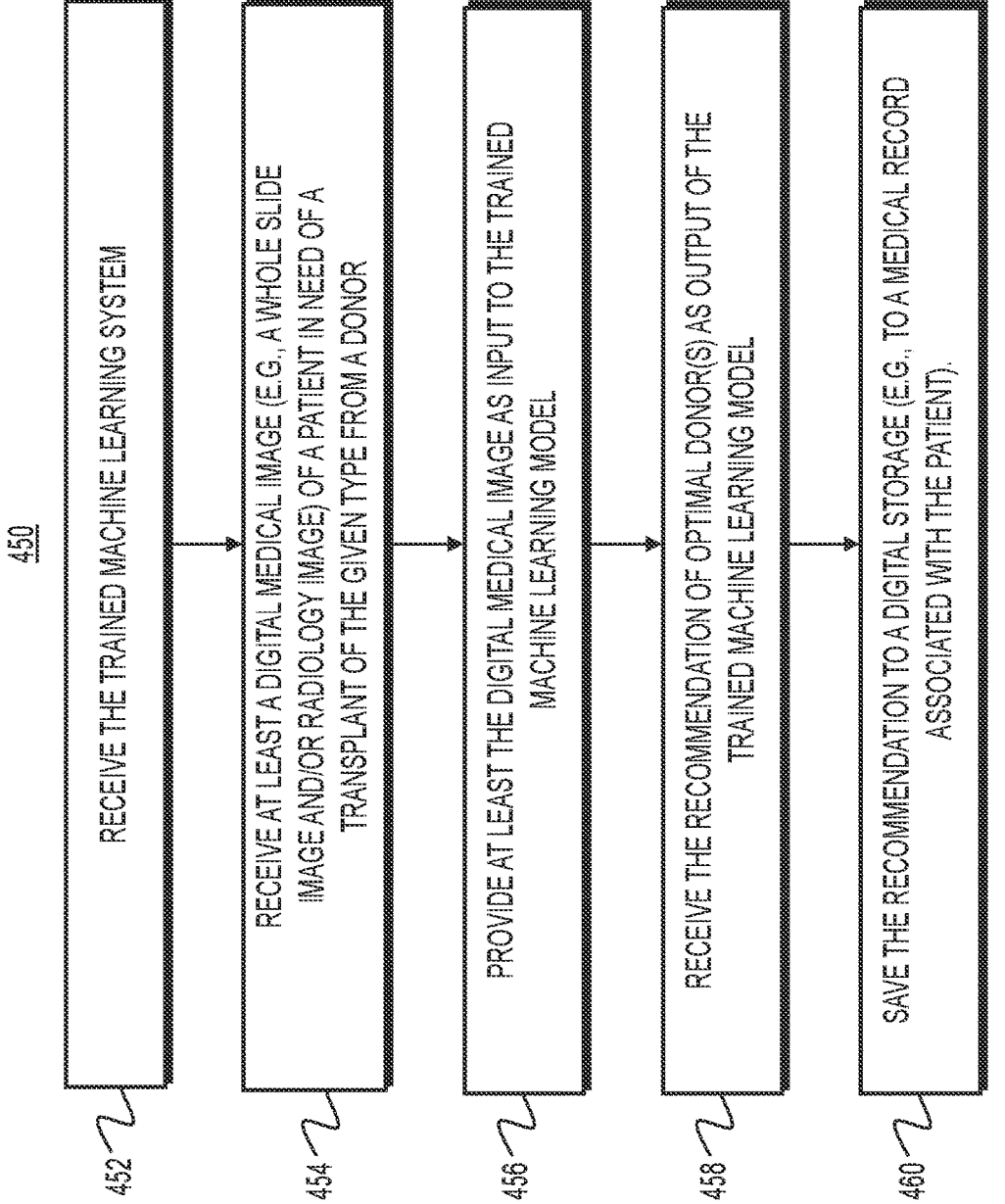

450

452 — RECEIVE THE TRAINED MACHINE LEARNING SYSTEM

454 — RECEIVE AT LEAST A DIGITAL MEDICAL IMAGE (E.G., A WHOLE SLIDE IMAGE AND/OR RADIOLOGY IMAGE) OF A PATIENT IN NEED OF A TRANSPLANT OF THE GIVEN TYPE FROM A DONOR

456 — PROVIDE AT LEAST THE DIGITAL MEDICAL IMAGE AS INPUT TO THE TRAINED MACHINE LEARNING MODEL

458 — RECEIVE THE RECOMMENDATION OF OPTIMAL DONOR(S) AS OUTPUT OF THE TRAINED MACHINE LEARNING MODEL

460 — SAVE THE RECOMMENDATION TO A DIGITAL STORAGE (E.G., TO A MEDICAL RECORD ASSOCIATED WITH THE PATIENT).

502 — RECEIVE TRAINING DATA, THE TRAINING DATA COMPRISING METADATA FOR A PLURALITY OF PATIENTS WHO HAD PREVIOUSLY RECEIVED/IMPLEMENTED LIFESTYLE RECOMMENDATIONS

504 — BUILD AND TRAIN A MACHINE LEARNING MODEL TO PREDICT A LIFESTYLE RECOMMENDATION USING THE TRAINING DATA

506 — SAVE THE TRAINED MACHINE LEARNING MODEL ELECTRONIC STORAGE

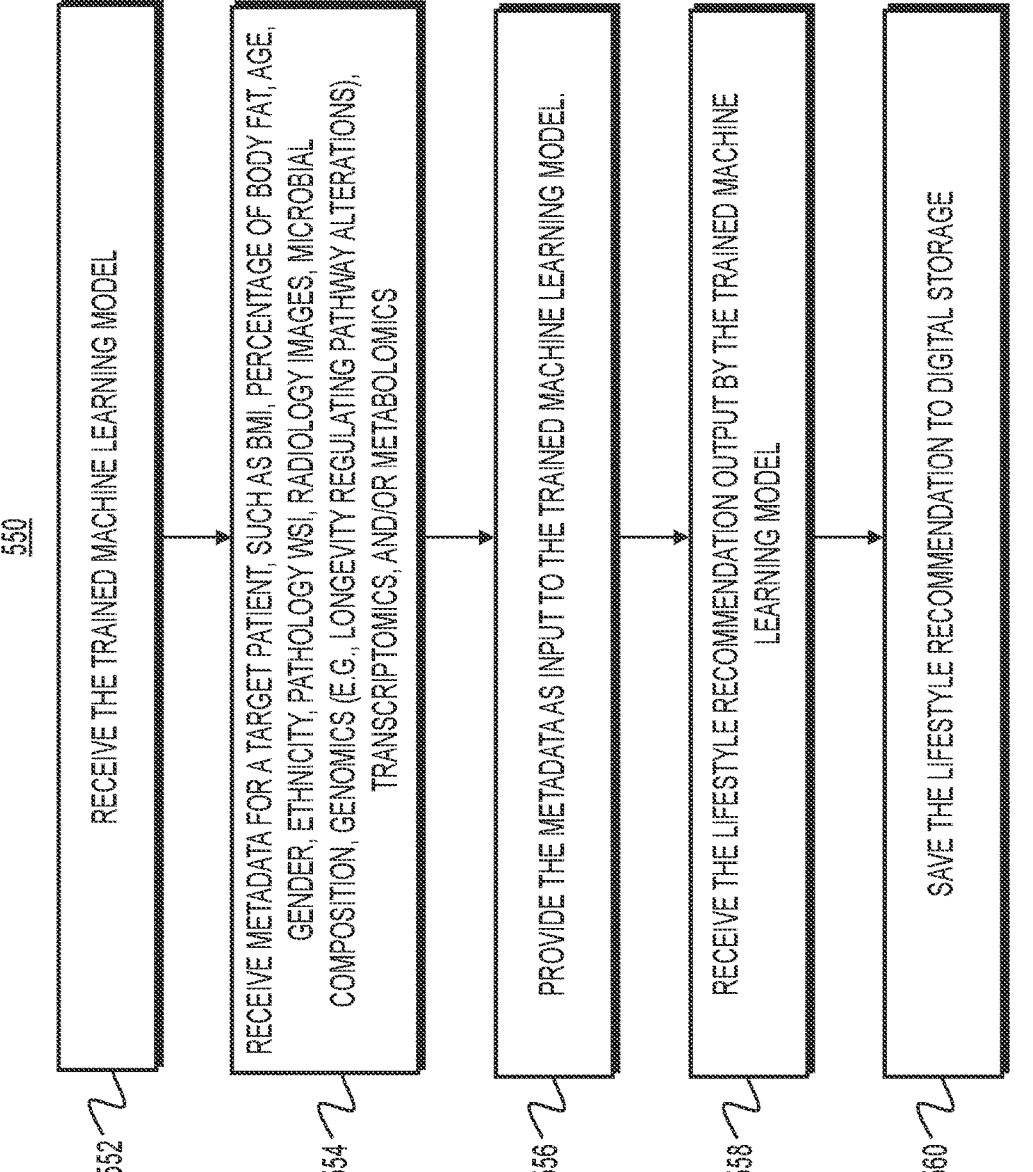

550

552 — RECEIVE THE TRAINED MACHINE LEARNING MODEL

554 — RECEIVE METADATA FOR A TARGET PATIENT, SUCH AS BMI, PERCENTAGE OF BODY FAT, AGE, GENDER, ETHNICITY, PATHOLOGY WSI, RADIOLOGY IMAGES, MICROBIAL COMPOSITION, GENOMICS (E.G., LONGEVITY REGULATING PATHWAY ALTERATIONS), TRANSCRIPTOMICS, AND/OR METABOLOMICS

556 — PROVIDE THE METADATA AS INPUT TO THE TRAINED MACHINE LEARNING MODEL

558 — RECEIVE THE LIFESTYLE RECOMMENDATION OUTPUT BY THE TRAINED MACHINE LEARNING MODEL

560 — SAVE THE LIFESTYLE RECOMMENDATION TO DIGITAL STORAGE

*FIG. 5B*

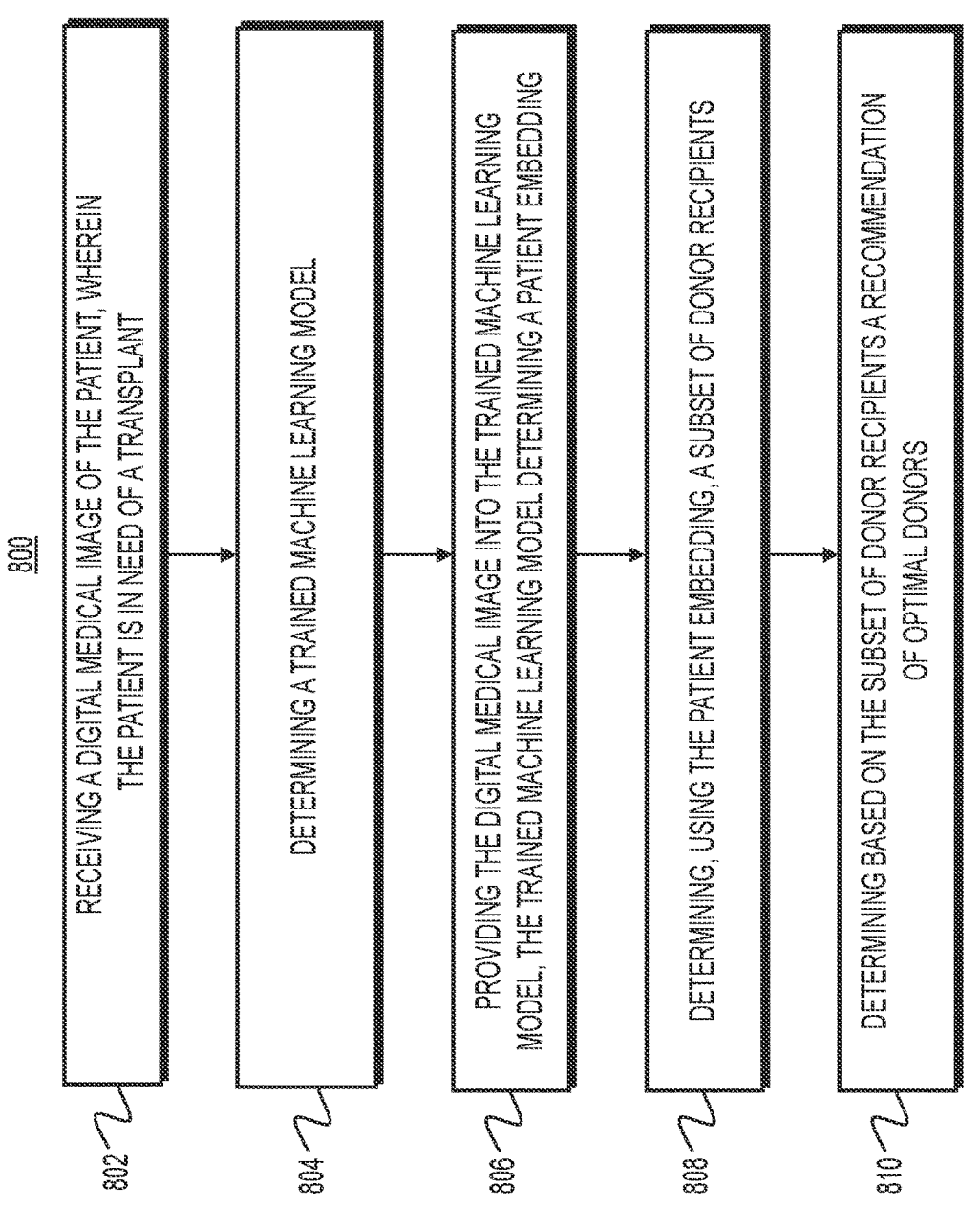

800

802 — RECEIVING A DIGITAL MEDICAL IMAGE OF THE PATIENT, WHEREIN THE PATIENT IS IN NEED OF A TRANSPLANT

804 — DETERMINING A TRAINED MACHINE LEARNING MODEL

806 — PROVIDING THE DIGITAL MEDICAL IMAGE INTO THE TRAINED MACHINE LEARNING MODEL, THE TRAINED MACHINE LEARNING MODEL DETERMINING A PATIENT EMBEDDING

808 — DETERMINING, USING THE PATIENT EMBEDDING, A SUBSET OF DONOR RECIPIENTS

810 — DETERMINING BASED ON THE SUBSET OF DONOR RECIPIENTS A RECOMMENDATION OF OPTIMAL DONORS

*FIG. 8*

SYSTEMS AND METHODS FOR PROCESSING ELECTRONIC IMAGES TO IDENTIFY TRANSPLANT DONOR-RECIPIENT MATCHES

CROSS-REFERENCE TO RELATED APPLICATION(S)

This application claims the benefit of priority to U.S. Provisional Patent Application No. 63/366,015, filed Jun. 8, 2022, the entirety of which is incorporated by reference herein.

FIELD OF THE DISCLOSURE

Various embodiments of the present disclosure pertain generally to processing electronic images. More specifically, particular embodiments of the present disclosure relate to systems and methods for processing electronic images, among other metadata, using artificial intelligence (AI) technology, machine learning, and/or image processing techniques to identity transplant donor-recipient matches.

BACKGROUND

Many diseases are treated by transplanting organs, tissues, or other foreign materials into a patient from a donor. As one example, a patient having a faulty organ due to disease, e.g., a faulty lung or heart due to lung or heart failure, may undergo an organ transplant to replace the faulty organ. As another example, a patient needing treatment for a gastrointestinal disease, such as recurrent *Clostridium difficile* colitis, may undergo a fecal microbiota transplantation (FMT), also referred to as bacteriotherapy, where stool from a healthy donor is transferred into the gastrointestinal tract of the patient. Additionally, ongoing studies are investigating bacteriotherapy's efficacy for treating other diseases, such as obesity, overall health, cancer, and non-alcoholic fatty liver disease. However, identifying the optimal donor for treating the patient's disease and ensuring that the patient benefits is challenging, and a failure to do so my lead to severe, life-threatening consequences for the patient.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the present disclosure, systems and methods are disclosed for processing electronic medical images. In one aspect, a computer-implemented method for processing electronic medical images to predict one or more donor recipients for a patient. The method may comprise: receiving a digital medical image of the patient, wherein the patient is in need of a transplant; determining a trained machine learning system; providing the digital medical image into the trained machine learning system, the trained machine learning system determining a patient embedding; determining, using the patient embedding, a subset of donor recipients; and determining based on the subset of donor recipients a recommendation of optimal donors.

The transplant may be a fecal matter transplant. The transplant may be a liver transplant. A salient region detection module may be applied to determine a saliency of each region within the received digital medical image, and non-salient image regions are excluded from processing by the trained machine learning system. Metadata associated with the patient may be received, the metadata including: clinical data, genetic information, microbial composition, and/or life history data; and the metadata may be provided into the trained machine learning system.

A second trained machine learning system may be determined, the second trained machine learning system being capable of determining a dietary, sleep, or exercise suggestion, wherein the second trained machine learning system receives as input the digital medical image of the patient, determines a lifestyle embedding, and determines, based on the lifestyle embedding, a dietary, sleep, or exercise suggestion for the patient.

Donor collection entities may be notified, with a notification, of a need for donors with a given profile. The notification may include metadata of the patient in need, an indication of the donor profile needed that matches the recipient, and/or a request for the donor collection entities to start collecting donors that have a similar profile.

According to certain aspects of the present disclosure, systems and methods are disclosed for processing electronic medical images. In another aspect, a system for processing electronic digital medical images may comprise at least one memory storing instructions and at least one processor configured to execute the instructions to perform operations. The system for processing electronic digital medical images may predict one or more donor recipients for a patient. The at least one processor may comprise: receiving a digital medical image of the patient, wherein the patient is in need of a transplant; determining a trained machine learning system; providing the digital medical image into the trained machine learning system, the trained machine learning system determining a patient embedding; determining, using the patient embedding, a subset of donor recipients; and determining based on the subset of donor recipients a recommendation of optimal donors.

According to certain aspects of the present disclosure, systems and methods are disclosed for processing electronic medical images. In another aspect, a non-transitory computer-readable medium storing instructions that, when executed by a processor, perform operations processing electronic digital medical images, is disclosed. The operations may predict one or more donor recipients for a patient. The operations may comprise: receiving a digital medical image of the patient, wherein the patient is in need of a transplant; determining a trained machine learning system; providing the digital medical image into the trained machine learning system, the trained machine learning system determining a patient embedding; determining, using the patient embedding, a subset of donor recipients; and determining based on the subset of donor recipients a recommendation of optimal donors.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims. As will be apparent from the embodiments below, an advantage to the disclosed systems and methods is that multiple parties may fully utilize their data without allowing others to have direct access to raw data. The disclosed systems and methods discussed below may allow advertisers to understand users' online behaviors through the indirect use of raw data and may maintain privacy of the users and the data.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3A is a flowchart illustrating an example method of training an algorithm for region detection, according to an exemplary embodiment of the present disclosure.

FIG. 4B is a flowchart illustrating an exemplary method of utilizing a donor recipient prediction according to an exemplary embodiment of the present disclosure.

FIG. 5B is a flowchart illustrating an exemplary method of utilizing a dietary, lifestyle, and lifespan recommendation module according to an exemplary embodiment of the present disclosure.

FIG. 8 illustrates an exemplary flowchart for processing images to determine a donor recipient prediction, according to techniques presented herein.

DESCRIPTION OF THE EMBODIMENTS

Figure 1A:
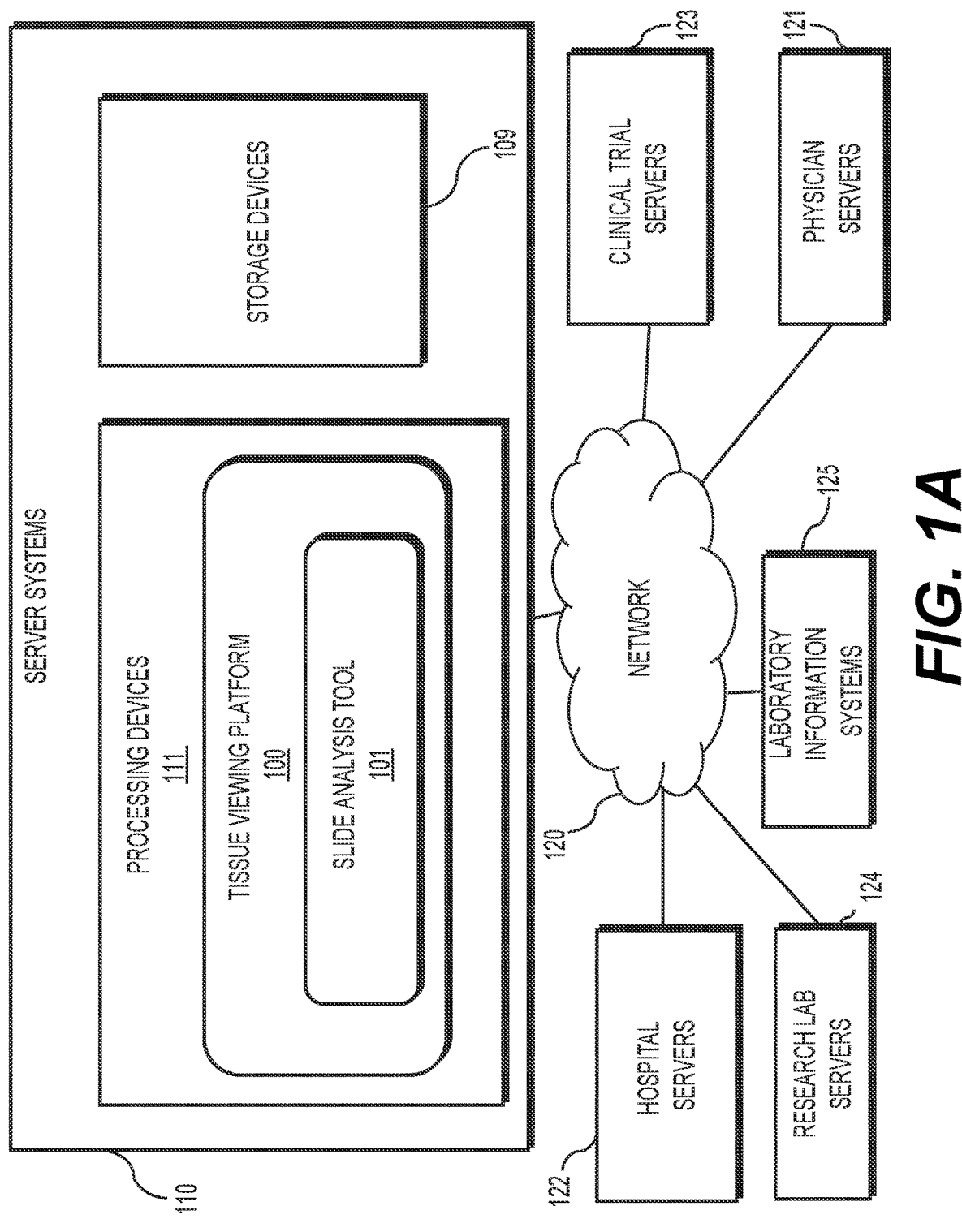
FIG. 1A illustrates an exemplary block diagram of a system and network for processing images to determine a donor recipient prediction, according to techniques presented herein.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Transplants of tissue, organs, or foreign matter into a patient for treating disease is common. Exemplary forms of transplantation from donors to patients include: microbial bioflora transplantation, e.g., fecal microbiota transplantation (FMT), which is done by having banks of fecal samples from donors; organ transplantation from living donors, which occurs when an organ can be removed from a donor without death, e.g., removal of a kidney or a portion of the liver; organ transplantation from deceased or brain-dead donors, which includes critical organs such as the heart and lungs that are viable for about 24 hours after the donor's death; and tissue transplantation from a deceased or brain-dead donor, including bones, skin, heart valves, nerves, corneas, and veins, which may be preserved in a tissue bank for up to five years. In some examples, transplant donors may also include animals, such as pigs.

Although transplants of tissues, organs, or foreign matter into a patient are common, identifying donor tissues, organs, or foreign matter that lead to a best outcome is challenging. Techniques discussed herein may use AI technology, machine learning, and/or image processing tools applied to patient and donor data, e.g., digital images of histology slides, radiology, clinical reports, genetic information, microbial composition, life history, etc., to identify optimal donors for a patient in need of a transplant. These techniques include, but are not limited to, identifying optimal donors for FMT and identifying optimal donors for organ transplantation. In some examples, the identification of optimal donors for the patient may be one filter (e.g., one data point) implemented by a medical professional when determining candidate donors for a transplant that may, e.g., increase a confidence of the medical professional in selecting a most optimal candidate donor that will provide a best outcome for the patient. Additional techniques discussed herein may use AI technology, machine learning, and image processing tools to provide dietary, lifestyle, and/or lifespan recommendations to improve a transplant patient's outcome ad/or to further optimize the donor-patient match. Further techniques discussed herein may automatically notify donor collection entities of donor types needed for (e.g., to match) transplant patients.

FIG. 1A illustrates a block diagram of a system and network for processing images to determine a determine a donor recipient prediction, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present disclosure, the electronic network 120 may also be connected to server systems 110, which may include processing devices 111 that are configured to implement a tissue viewing platform 100, which includes a slide analysis tool 101 for determining specimen property or image property information pertaining to digital pathology image(s), and using machine learning to classify a specimen, according to an exemplary embodiment of the present disclosure. The tissue viewing platform 100 may also include a donor recipient inference tool 141 for determining a donor recipient prediction. In other examples, the donor recipient inference tool 141 may be operated separately from (e.g., by a different platform than) the tissue viewing platform 100. The tissue viewing platform 100 may also include a dietary and lifestyle tool 144 for determining a dietary, lifestyle, and/or lifespan recommendation. In other examples, the dietary and lifestyle tool 144 may be operated separately from (e.g., by a different platform than) the tissue viewing platform 100.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include a machine learning tool for a tissue viewing platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in one of the laboratory information systems 125.

Figure 1B:
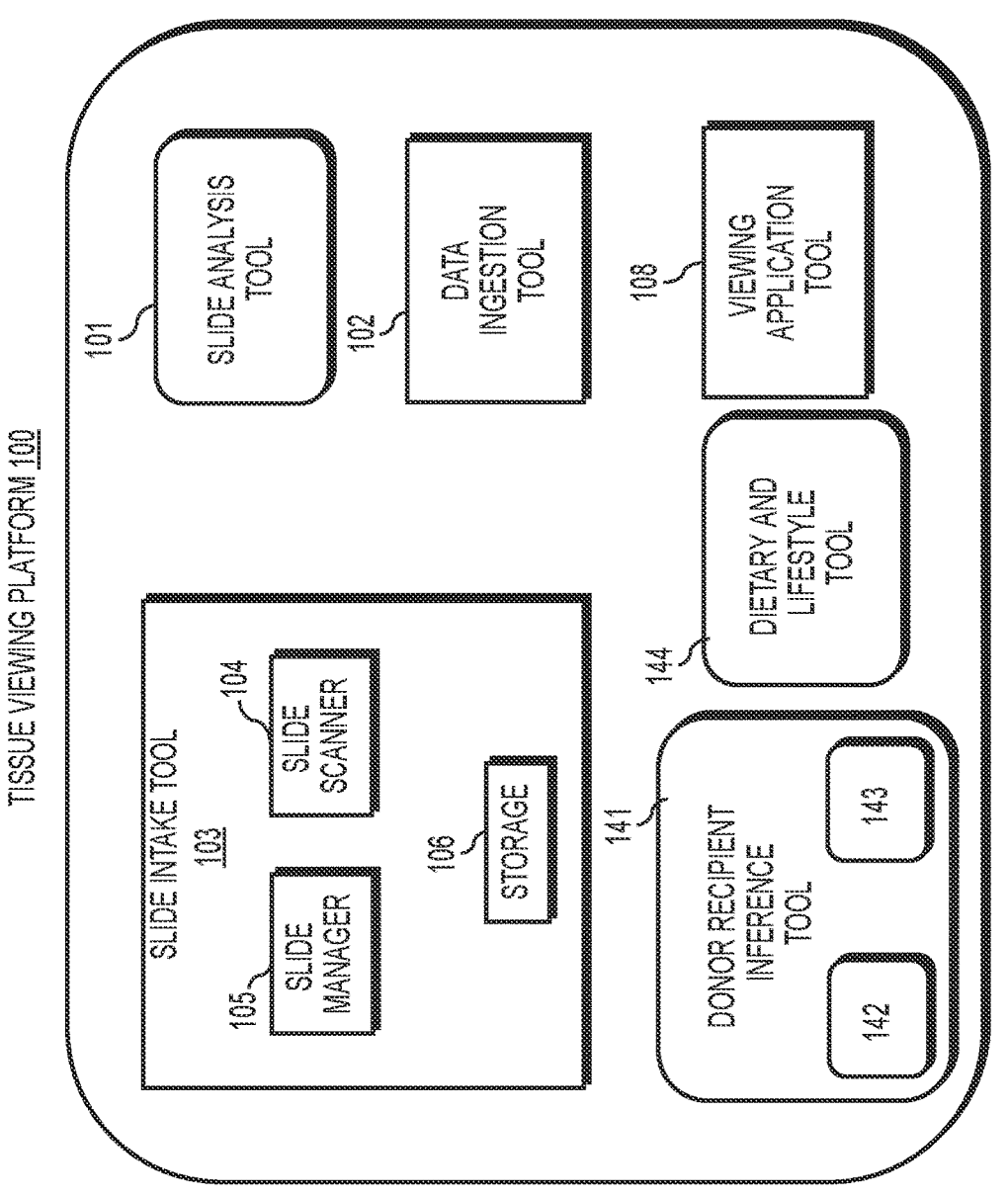
FIG. 1B illustrates an exemplary block diagram of a tissue viewing platform according to techniques presented herein.

FIG. 1B illustrates an exemplary block diagram of the tissue viewing platform 100. For example, the tissue viewing platform 100 may include a slide analysis tool 101, a donor recipient inference tool 141, a dietary and lifestyle tool 144, a data ingestion tool 102, a slide intake tool 103, a slide scanner 104, a slide manager 105, a storage 106, and a viewing application tool 108.

The slide analysis tool 101, as described below, refers to a process and system for processing digital images associated with a tissue specimen (e.g., digitized images of slide-mounted histology or cytology specimens), and using machine learning to analyze a slide, according to an exemplary embodiment.

The donor recipient inference tool 141, as described in greater detail below, refers to a process and system for processing digital pathology slides (e.g., digitalized images of a slide-mounted history or cytology specimens) and/or metadata, and using machine learning or a rules based system for determining a patient embedding, a subset of recipients, and an optimal donor prediction. The trained system may have two parts, a embedding tool 142 and a donor recommendation tool 143, embedding tool 142 determining patient embeddings, and the donor recommendation tool 143 may determine one or more donor recommendation based on the determined patient embedding.

The dietary and lifestyle tool 144, as described in greater detail below, refers to a process and system for processing digital pathology slides (e.g., digitalized images of a slide-mounted history or cytology specimens) and/or metadata, and using machine learning or a rules based system for determining a lifestyle recommendation.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, donor recipient inference tool 141, and dietary and lifestyle tool 144 and each of their components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include one or more storage devices 109 for storing images and data received from at least one of the slide analysis tool 101, the donor recipient inference tool 141, the dietary and lifestyle tool 144, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools and modules may be located on a device that may be connected to an electronic network 120, such as the Internet or a cloud service provider, through one or more computers, servers, and/or handheld mobile devices.

Figure 1C:
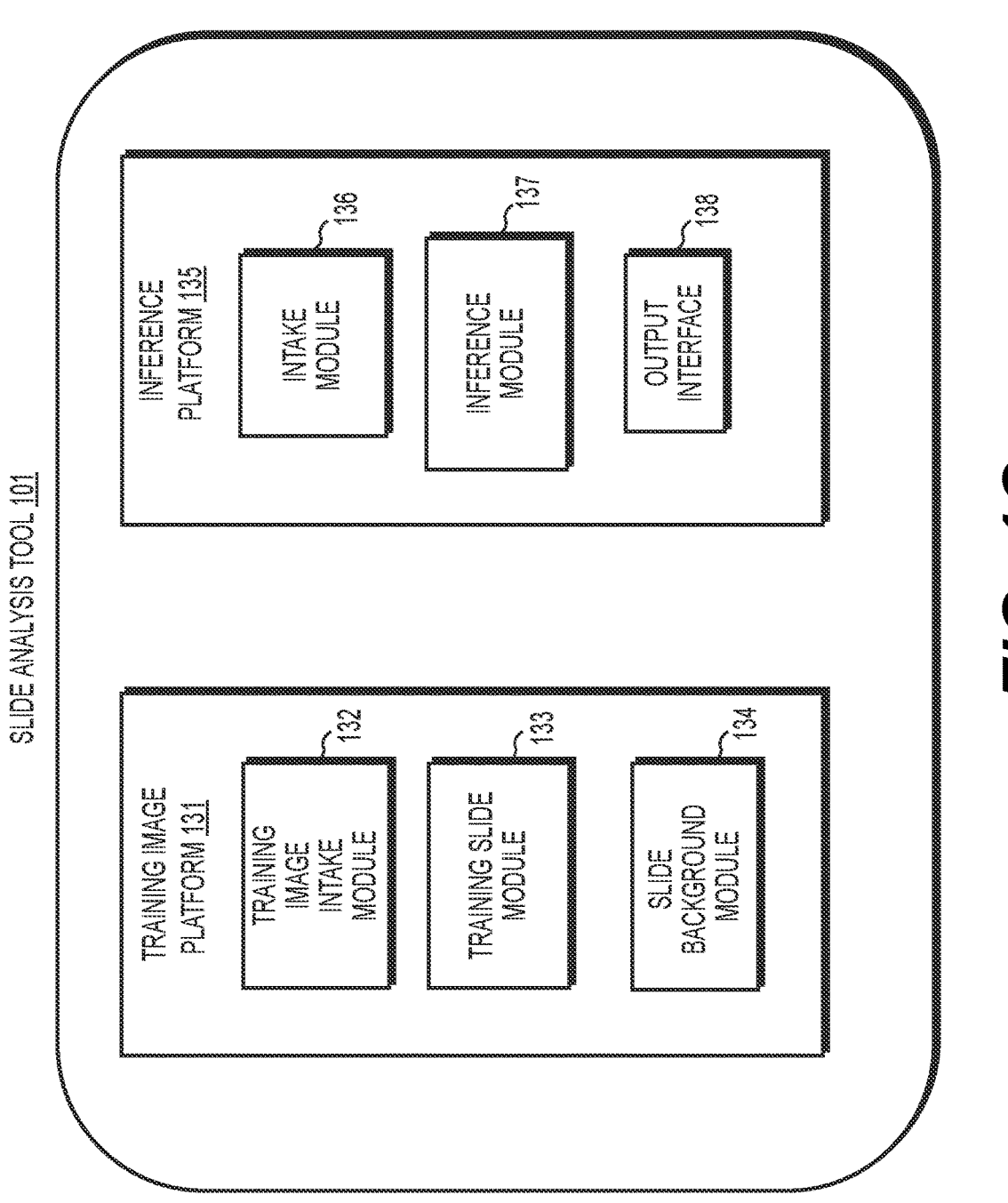
FIG. 1C illustrates an exemplary block diagram of a slide analysis tool, according to techniques presented herein.

FIG. 1C illustrates an exemplary block diagram of a slide analysis tool 101, according to an exemplary embodiment of the present disclosure. The slide analysis tool may include a training image platform 131 and/or an inference platform 135.

The training image platform 131, according to one embodiment, may create or receive training images that are used to train a machine learning system to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized image samples from a 3D imaging device, such as micro-CT.

The training image intake module 132 may create or receive a dataset comprising one or more training images corresponding to either or both of images of a human and/or animal tissue and images that are graphically rendered. For example, the training images may be received from any one or any combination of the server systems 110, physician servers 121, and/or laboratory information systems 125. This dataset may be kept on a digital storage device. The training slide module 133 may intake training data that includes images and corresponding information. For example, training slide module 133 training data may include receiving one or more images (e.g., WSIs) of a human or animal. This dataset may be kept on a digital storage device. In some examples, the dataset may be comprised of a plurality of data subsets, where each data subset corresponds to a training case from a plurality of training cases and includes one or more training images from the training case. The training slide module 133 may include one or more computing devices capable of, e.g., determining whether the training images have a sufficient level-of-quality for training a machine learning model. The training slide module 133 may further include one or more computing devices capable of, e.g., identifying whether a set of individual cells belong to a cell of interest or a background of a digitized image.

The slide background module 134 may analyze images of tissues and determine a background within a digital pathology image. It is useful to identify a background within a digital pathology slide to ensure tissue segments are not overlooked.

According to one embodiment, the inference platform 135 may include an intake module 136, an inference module 137, and an output interface 138. The inference platform 135 may receive a plurality of electronic images/additional information and apply one or more machine learning model to the received plurality of electronic images/information to extract relevant information and integrate spatial and orientation information for display on medical digital images. For example, the plurality of electronic images or additional information may be received from any one or any combination of the server systems 110, physician servers 121, hospital servers 122, clinical trial servers 123, research lab servers 124, and/or laboratory information systems 125. The intake module 136 may receive WSI's corresponding to one or more patients/individuals. Further, the WSI's may correspond to an animal. The inference module 137 may apply one or more machine learning models to a group of WSI and any additional information in order to extract relevant information and integrate spatial and orientation information for display on medical images. The inference module 137 may further incorporate the spatial characteristics of the salient tissue into the prediction.

The output interface 138 may be used to output information about the inputted images and additional information (e.g., to a screen, monitor, storage device, web browser, etc.). The output information may include information related to ranking causes of death. Further, output interface 138 may output WSI's that indicate locations/salient regions that include evidence related to outputs from inference module 137.

Techniques discussed herein may use AI technology, machine learning, and/or image processing tools applied to patient and donor data, e.g., digital images of histology slides, radiology, clinical reports, genetic information, microbial composition, life history, etc., to identify optimal donors for a patient in need of a transplant.

Figure 2:
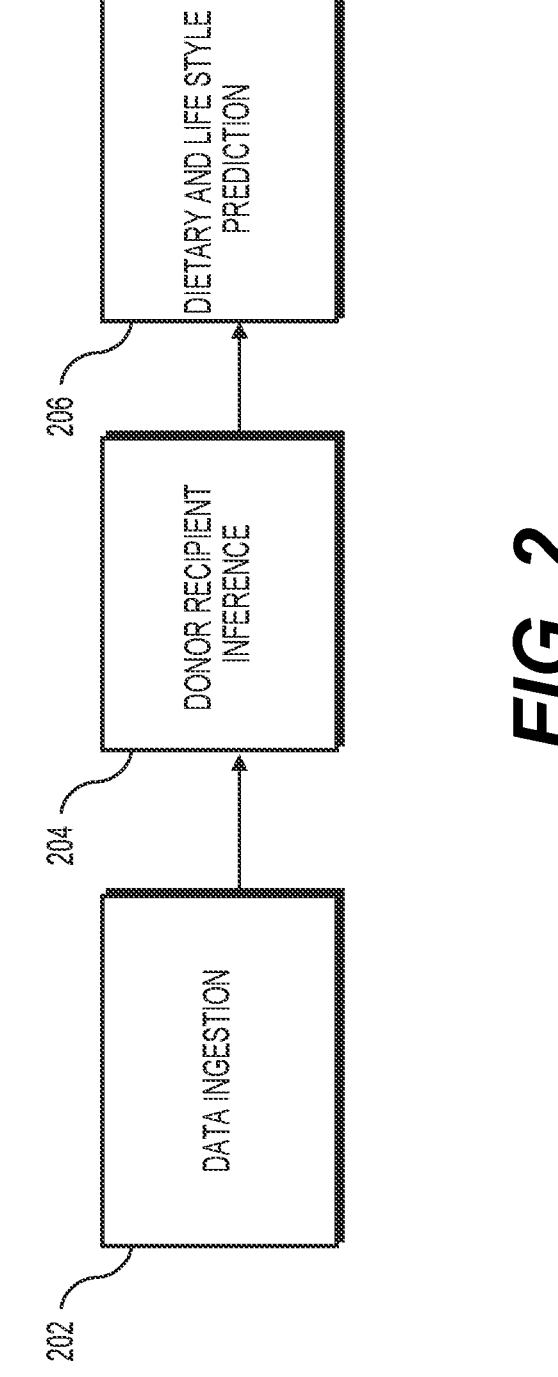
FIG. 2 illustrates an exemplary process for to determining a donor recipient prediction, according to techniques presented herein.

FIG. 2 illustrates an exemplary process 200 for to determining a donor recipient prediction, according to techniques presented herein. The systems and methods disclosed herein may include data ingestion 202, a donor recipient inference module 204, and a dietary and lifestyle prediction module 206. The process described in FIG. 2 may be performed by the slide analysis tool 101, the donor recipient inference tool 141, and/or the dietary and lifestyle tool 144. In other examples, aspects of the system described in FIG. 2 may be performed in external systems and received by the tissue viewing platform 100.

In FIG. 2, the system may first include data ingestion 202. Data ingestion 202 may be performed by the slide analysis tool 101. Data ingestion may include receiving one or more digital images (e.g., whole slide image (WSI) of histopathological slide, magnetic resonance imaging (MRI), computed tomography (CT), positron emission tomography (PET), mammogram, ultrasound, X-rays, photographs of external anatomy, etc.) into a digital storage device 109 (e.g., hard drive, network drive, cloud storage, RAM, etc.). The digital medical images may include at least digital medical images of transplant recipients (e.g., patients having previously received transplants from donors). The digital medical images may, in some examples, also include digital medical images of transplant donors. The digital medical images may, in some examples, also include digital medical images of individuals that may need a transplant. The digital medical images may be digital medical images of human tissues, organs, or other foreign matter associated with the transplant, for example, and/or animal tissues, organs, or other foreign matter (e.g., pig tissue, pig valves) that may be transplanted into humans as part of the transplant procedure. Optionally, metadata associated with the recipient and/or donor can also be ingested, e.g., metadata such as body mass index (BMI), percentage of body fat, age, gender, ethnicity, microbial composition, genomics (e.g., longevity regulating pathway alterations), transcriptomics, metabolomics, ancillary test results, etc. For training the machine learning system, each image may be paired with information from the donors and/or recipient, including whether the given transplant from the donor to the recipient was successful or not. Optionally, at least the digital medical images of the data ingested may be pre-processed. For example, one or more areas of tissue present in a digital medical image that may have been affected by the tissue biopsy or extraction procedure may be excluded. As one illustrative example, during the tissue biopsy, the surgeon performing the biopsy may introduce foreign microbes when cutting into the tissue. The area where the foreign microbes are introduced may be removed from the digital image during pre-processing to prevent the presence of the foreign microbes from interfering with the analysis of the image (e.g., by salient region detection module and/or the donor recipient inference tool 141, described below).

Next, data from the data ingestion 202 may be inserted into a salient region detection module described in greater detail below in FIGS. 3A and 3B. A salient region detection module, as further described below, may be used to identify the salient regions to be analyzed for each digital image. This may be done manually by a human or automatically using AI. An entire image or specific image regions can be considered salient. Salient region determination techniques are discussed in U.S. application Ser. No. 17/313,617, which is incorporated by reference herein in its entirety.

Next, the digital medical images from the data ingestion 202, which may or not have had a salient region identified, may be fed to a donor recipient inference module 204 (e.g., the donor recipient inference tool 141). The donor recipient inference module 204 that may implement a trained machine learning model to predict one or more optimal donors for a patient in need of a transplant. The model may incorporate spatial information from disparate regions in a digital medical image of the patient (e.g. may produce an embedding representing attributes of the patient in an embedding space) to facilitate the prediction. The prediction may output to an electronic storage device.

Next, the digital medical images from the data ingestion 202, which may or not have had a salient region identified and may or may not have had the donor recipient inference module 204 applied, are fed to a dietary and lifestyle prediction module 206 (e.g., the dietary and lifestyle tool 144). The dietary and lifestyle prediction module 206 may implement a trained machine learning model to predict one or more predict lifestyle recommendations. The model may incorporate spatial information from disparate regions in a digital medical image of the patient (e.g. may produce an embedding representing attributes of the patient in an embedding space) as well as received metadata to facilitate the prediction. The prediction is output to an electronic storage device.

The optional salient region detection module, the donor recipient inference module 204, and the dietary and lifestyle prediction module 206 are described in turn below.

One aspect of the systems and methods disclosed herein includes the automatic identification of one or more salient regions to be analyzed for a digital image using AI. This may be performed by a salient region detection module. An entire image or specific image regions may be considered salient.

A continuous score of interest may be specific to certain structures within the digital image, and it can be important to identify relevant regions so that they can be included while excluding irrelevant ones. For example, with MRI, PET, or CT data localizing a specific organ of interest could be needed. Salient region identification can enable the downstream machine learning system to learn how to detect morphologies from less annotated data and to make more accurate predictions.

The salient region detection module can output a salient region that was specified by a human annotator using an image segmentation mask, a bounding box, line segment, point annotation, freeform shape, or a polygon, or any combination of the aforementioned. Alternatively, this module can be created using machine learning to identify the appropriate locations.

As described in more detail below with respect to the steps performed to train one or more machine learning systems to identify one or more salient regions of a digital image, there are two general approaches to using machine learning to create a salient region detector. The first approach includes strongly supervised methods that identify precisely where the morphology of interest could be found. The second approach includes weakly supervised methods that do not provide a precise location.

For strongly supervised training, the system needs the image and the location of the salient regions that could potentially express the biomarker as input. For 2D images, e.g., whole slide images (WSI) in pathology, these locations could be specified with pixel-level labeling, bounding box-based labeling, polygon-based labeling, or using a corresponding image where the saliency has been identified (e.g., using immunohistochemical (IHC) staining). For 3D images, e.g., CT and MRI scans, the locations could be specified with voxel-level labeling, using a cuboid, etc. or use a parameterized representation allowing for subvoxel-level labeling, such as parameterized curves or surfaces, or deformed template. For weakly supervised training, the system requires the image or images and the presence/absence of the salient regions, but the exact location of the salient location does not need to be specified.

The training of the salient region detection module discussed in FIG. 2 may be described in greater detail below. Examples of training the salient region detection module may include method 300 of FIG. 3A. Examples of using the salient region detection module may include method 350 of FIG. 3B.

FIG. 3A is a flowchart illustrating an example method 300 of training an algorithm for region detection, according to an exemplary embodiment of the present disclosure. The method 300 of FIG. 3A depicts steps that may be performed by, for example, the slide analysis tool 101 as described above in FIG. 1C. Alternatively, the method may be performed by an external system. According to one example aspect, for training the one or more machine learning systems to identify one or more salient regions of a digital image, the following method 300 may be performed:

At step 302, the system may receive one or more digital images of a medical specimen (e.g., histopathological slide images, CT, MRI, PET, mammogram, ultrasound, X-rays, photographs of external anatomy, etc.) into a digital storage device (e.g., hard drive, network drive, cloud storage, RAM, etc.) and an indication of the presence or absence of the salient region (e.g., a particular organ, tissue, region of tissue, etc.) within the image.

At step 304, the system may, break each digital image into sub-regions that will then have their saliency determined. Regions can be specified in a variety of methods, including creating tiles of the image, segmentations based on edge/contrast, segmentations via color differences, segmentations based on energy minimization, supervised determination by the machine learning model, EdgeBoxes, etc.

At step 306 a machine learning system may be trained that takes as input a digital image and predicts whether the salient region is present or not. Training the salient region detection module may also include training a machine learning system to receive, as an input, a digital image and to predict whether the salient region is present or not. Many methods may be used to learn which regions are salient, including but not limited to weak supervision, bounding box or polygon-based supervision, or pixel-level or voxel-level labeling.

Weak supervision may involve training a machine learning model (e.g., multi-layer perceptron (MLP), convolutional neural network (CNN), transformers, graph neural network, support vector machine (SVM), random forest, etc.) using multiple instance learning (MIL). The MIL may use weak labeling of the digital image or a collection of images. The label may correspond to the presence or absence of a salient region.

Bounding box or polygon-based supervision may involve training a machine learning model (e.g., R-CNN, Faster R-CNN, Selective Search, etc.) using bounding boxes or polygons. The bounding boxes or polygons may specify sub-regions of the digital image that are salient for detection of the presence or absence of a biomarker.

Pixel-level or voxel-level labeling (e.g., semantic or instance segmentation) may involve training a machine learning model (e.g., Mask R-CNN, U-Net, fully convolutional neural network, transformers, etc.) where individual pixels and/or voxels are identified as being salient for the detection of continuous score(s) of interest. Labels could include in situ tumor, invasive tumor, tumor stroma, fat, etc. Pixel-level/voxel-level labeling may be from a human annotator or may be from registered images that indicate saliency.

Figure 3B:
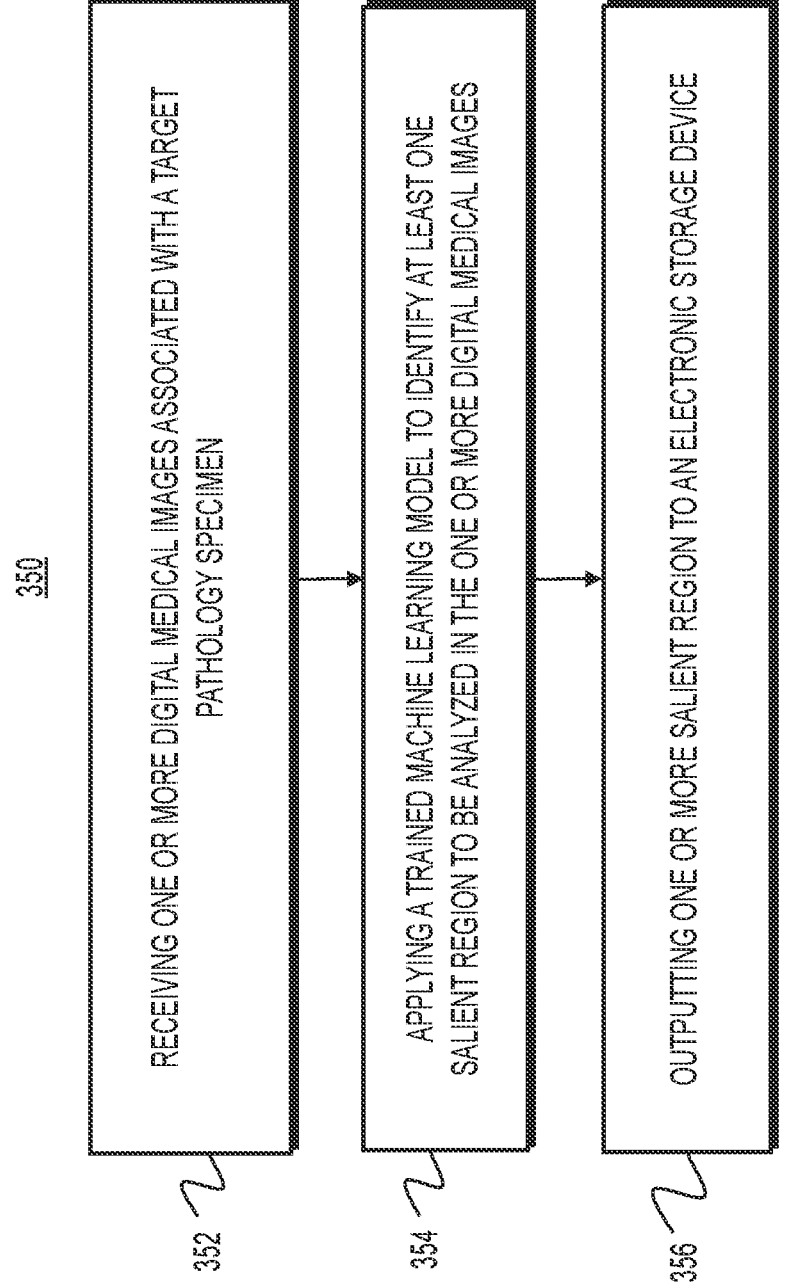
FIG. 3B is a flowchart illustrating an exemplary method of utilizing an algorithm for region detection, according to an exemplary embodiment of the present disclosure.

According to another example aspect, to implement the one or more trained machine learning systems for identifying one or more salient regions in a digital image, the following steps may be performed:

FIG. 3B is a flowchart illustrating methods 350 for how to provide image region detection, according to one or more exemplary embodiments herein. FIG. 3B may illustrate a method that utilizes the neural network that was trained in FIG. 3A. The exemplary method 350 (e.g., steps 352-356) of FIG. 3B depicts steps that may be performed by, for example, by the slide analysis tool 101. These steps may be performed automatically or in response to a request from a user (e.g., physician, pathologist, etc.). Alternatively, the method described in flowchart 350 may be performed by any computer process system capable of receiving image inputs such as device 900 and capable of including or importing the neural network described in FIG. 3A.

At step 352, a system may receive one or more digital medical images may be received of a medical specimen into a digital storage device (e.g., hard drive, network drive, cloud storage, RAM, etc.). Using the salient region detection module may optionally include breaking or dividing each digital image into sub-regions and determining a saliency (e.g., sub-regions of tissue which has morphology of interest) of each sub-region using the same approach from training step 304.

At step 354, the trained machine learning system from FIG. 3A may be applied to the inputted images to predict which regions of the image are salient and could potentially exhibit the continuous score(s) of interest.

At step 356, if salient regions are found at step 354, the system may identify the salient region locations and flag them. If salient regions are present, detection of the region can be done using a variety of methods, including but not restricted to: running the machine learning model on image sub-regions to generate the prediction for each sub-region; or using machine learning visualization tools to create a detailed heatmap, etc. Example techniques are described in U.S. application Ser. No. 17/016,048, filed Sep. 9, 2020, and Ser. No. 17/313,617, filed May 6, 2021, which are incorporated herein by reference in their entireties. The detailed heatmap may be created by using class activation maps, GradCAM, etc. Machine learning visualization tools may then be used to extract relevant regions and/or location information.

The salient regions may be any tissue regions. For example, the salient region could correspond to lamina propria (Mucous membrane), or submucosa.

The outputted salient regions from step 356 may then be fed into the donor recipient inference module 204. The training of the donor recipient inference module 204 may be described in greater detail below. Examples of training the donor recipient inference module 204 may include method 400 of FIG. 4A. Examples of using donor recipient inference module 204 may include method 450 of FIG. 4B.

Another aspect of donor recipient inference module 204 disclosed herein includes using AI technology, machine learning, and/or image processing techniques to identify one or more optimal donors for a patient in need of a transplant.

Figure 4A:
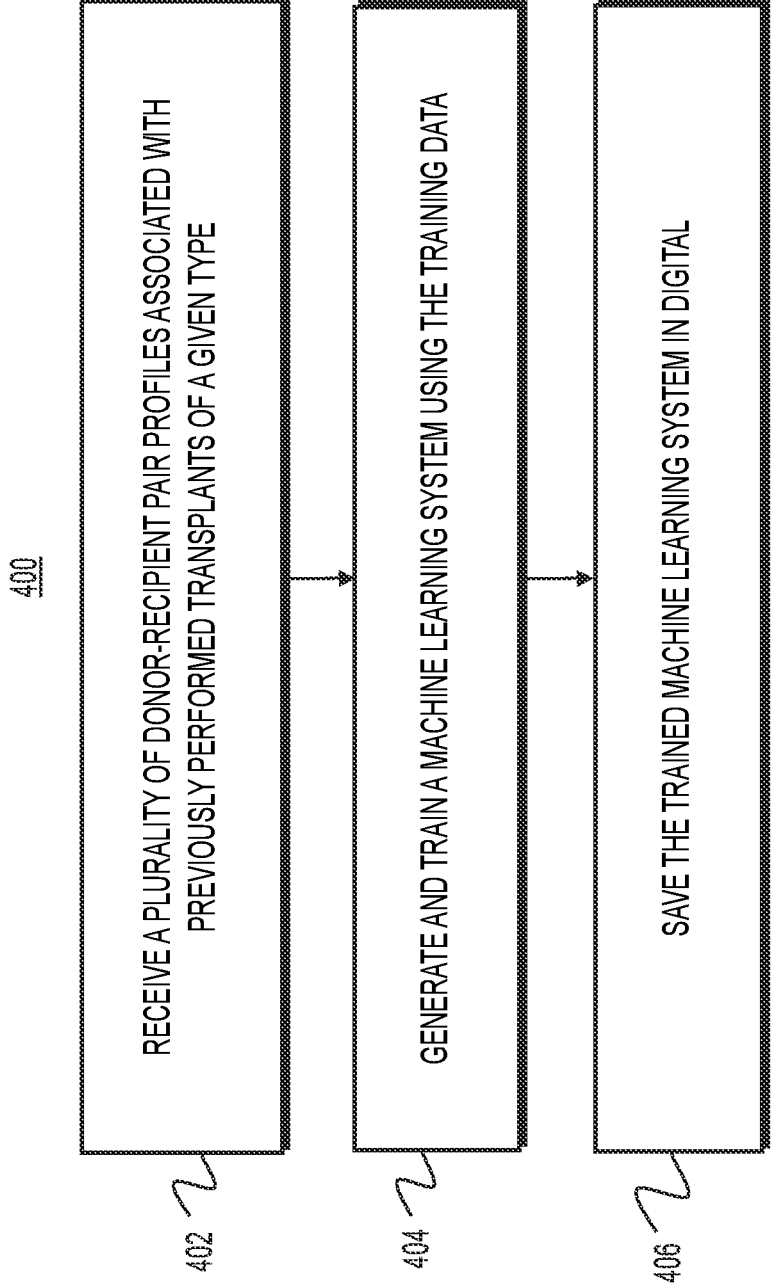
FIG. 4A is a flowchart illustrating an example method of training a donor recipient prediction module according to an exemplary embodiment of the present disclosure.

FIG. 4A is a flowchart illustrating an example method 400 of training a donor recipient inference module according to an exemplary embodiment of the present disclosure. The method 400 of FIG. 4A depicts steps that may be performed by, for example, the donor recipient inference tool 141 as described above. Alternatively, the method 400 may be performed by an external system.

According to one example aspect, for training a machine learning model to predict optimal transplant donors for a given transplant type, method 400 may be performed.

At step 402, the system may receive training data into a digital storage device 109 (e.g., hard drive, network drive, cloud storage, RAM, etc.). The training data may include a plurality of donor-recipient pair profiles associated with previously performed transplants of a given type. Each donor-recipient pair profile may include metadata associated with a donor of a transplant and a recipient of the transplant (e.g., oxygen at rest, pulmonary artery pressure, age, body mass index (BMI), total bilirubin), as well as an outcome of the transplant (e.g., successful or not successful, rejected or not rejected, graft survival or graft failure, survival time following transplantation, and other similar measures, including total lung capacity (TLC), peak oxygen consumption, and oxygen saturation). The particular types of metadata and/or outcome metrics may be based on a type of the transplant. In some examples, depending on a type of the transplant, a delivery type used for each donor-recipient pair profile may be included (e.g., for FMT, pill versus liquid). Information from the donor and recipient may either be an electronically documented text paragraph, structured data, imaging data or numbers that is stored in and received from a digital storage device (e.g., hard drive, network drive, cloud storage, RAM, etc.). Example types of metadata associated with the donor and/or the recipient of the transplant may include digital images (e.g., whole slide images of histopathological slides and/or radiological images), clinical data, genetic information, microbial composition, life history, and/or other similar data. For example, the digital images may be of intestinal tissue. The tissue may be of areas of a colon cecum, ascending, transverse, descending, sigmoid, or a rectum. In some examples, a portion of the metadata may be ingested to stratify and split the system for machine learning. The metadata may further include digital medical images of fecal matter. The plurality of donor-recipient pair profiles may be stored within a database for subsequent lookup and/or reference. At least a portion of the data from the plurality of donor-recipient pair profiles may be used as training data for a machine learning model.

Next, the salient region detection module described in FIGS. 3A and 3B may be applied to identify the saliency of each region within the digital medical images (e.g., of histology images) and exclude non-salient image regions from subsequent processing.

At step 404, the system may generate and train the machine learning system using the training data. The trained machine learning system may be located within the donor recipient inference tool 141. The trained system may have two parts, an embedding tool 142 and a donor recommendation tool 143, both located within the donor recipient inference tool 141. The machine learning model may be built and trained using the training data from step 402. For example, the machine learning model may output, for at least the recipients of the donor-recipient pair profiles, recipient embeddings based on the respective digital medical images and/or other metadata of the recipients in an embedding space (e.g., a vector). The recipient embeddings may be determined by the embedding tool 142. The recipient embeddings may indicate a plurality of attributes representing the respective recipients, such that recipients that share more similar attributes may be of a closer distance to one another in the embedding space. By representing at least each of the recipients as vectors in the embedding space through production of the embeddings, a donor recommendation system may be built for identifying optimal transplant donor-recipient matches. The donor recommendation system may be performed by the donor recommendation tool 143. The donor recommendation tool 143 may receive as input embeddings determined by the embedding tool 142. In some examples, either the embedding tool 142 or the donor recommendation tool 143 may be located on an external server and accessed through network 120. Further, embedding tool 142 and donor recommendation tool 143 may be two separate machine learning systems that are trained separately.

For example, for a patient in need of a transplant, the trained machine learning model may produce a patient embedding in the embedding space and identify similar recipients to the patient having recipient embeddings close in distance from the patient embedding in the embedding space. If those identified similar recipients had a successful transplant from the donors of the respective donor-recipient pair profiles, the system may infer that those donors may also provide an optimal match to the patient in need of the transplant (e.g., result in a successful transplant outcome for the patient). In some examples, the machine learning model(s) are trained using a semi-supervised, multiple instance learning approach. In other examples, other machine learning approaches (e.g., supervised, unsupervised, semi-supervised) may be utilized. Additionally or alternatively, when the metadata of the donors of the donor-recipient pair profiles are included as training data, the machine learning model may output donor embeddings for the donors based on the respective digital images and/or other metadata in the embedding space. The donor embeddings may similarly indicate a plurality of attributes representing the respective donors. In such examples, for a patient in need of a transplant, the trained machine learning model may produce a patient embedding in the embedding space and identify donors similar to the patient (e.g., donors having donor embeddings closest in distance to the patient embedding in the embedding space). Based on the similarity between the patient and the donors, the system may infer that those donors may provide an optimal match to the patient in need of the transplant (e.g., result in a successful transplant outcome for the patient).

At step 406, the trained machine learning system may be saved in digital storage (e.g., digital storage 109) for subsequent use.

FIG. 4B is a flowchart illustrating an exemplary method of performing a donor recipient inference according to an exemplary embodiment of the present disclosure. The exemplary method 450 (e.g., steps 452-460) of FIG. 4B depicts steps that may be performed by, for example, by the donor recipient inference tool 141. These steps may be performed automatically or in response to a request from a user (e.g., physician, pathologist, etc.). These steps may describe an exemplary method of how to use the trained system described in FIG. 4A. Alternatively, the method described in flowchart 450 may be performed by any computer process system capable of receiving image inputs such as device 900 and capable of including or importing the neural network described in FIG. 4A.

According to one example aspect, to implement the trained machine learning model to predict optimal transplant donors for a given transplant type, the method 450 may be performed.

At step 452, the system may determine a trained machine learning system. For example, the trained learning system may be the machine learning system described in FIG. 4A. The trained system may perform a donor recipient inference. In one example, the trained system may be implemented by the donor recipient inference tool 141. In another example, the trained machine learning system may be imported through network 120.

At step 454, the system may receive at least a digital medical image (e.g., a whole slide image and/or radiology image) of a patient in need of a transplant of the given type from a donor. The digital medical image may include at least a tissue, or other anatomical structure associated with the transplant. For example, if the transplant is an FMT, colon tissue may be biopsied, and a histopathological slide may be prepared and imaged. As another example, if the transplant is a liver transplant, liver tissue may be biopsied, and a histopathological slide may be prepared and imaged. In another example, the trained system may also receive a digital medical image of fecal matter. Optionally, additional metadata associated with the patient may be received, such as clinical data, genetic information, microbial composition, life history (including current lifestyle), and/or other similar data.

Next, the trained system may apply the salient region detection module described in FIGS. 3A and 3B to identify the saliency of each region within the digital medical image received and exclude non-salient image regions from subsequent processing.

At step 456, the digital medical image and/or the metadata from step 454 may be received by the trained machine learning model received at step 452. The trained machine learning model may produce a patient embedding in the embedding space based on the digital medical image. If the additional metadata is optionally received, the trained machine learning model may also produce the patient embedding based on the additional metadata. Using the patient embedding, the trained machine learning model may identify a subset of recipients (e.g., from the recipients of the donor-recipient profile pairs having previously received a transplant of the given type) that are similar to the patient. For example, the subset of recipients identified may include one or more recipients having recipient embedding(s) within a threshold distance of the patient embedding in the embedding space. In some examples, the subset of recipients identified as being similar to the patient may be further refined to exclude those recipients whose transplant was not successful. The one or more donors of the transplants for the one or more recipients remaining in the further refined subset may be identified as optimal donor(s) (e.g., the donors identified by referencing the database storing the donor-recipient pair profiles) and output as a recommendation. This recommendation may be referred to as a donor recipient inference. In examples where digital medical images of the donors are received and used to produce donor embeddings in the embedding space, in addition to or rather than identifying similar recipients, similar donors may be identified. For example, one or more donors having donor embedding(s) within a threshold distance of the patient embedding in the embedding space may be identified.

At step 458, the system may receive the recommendation of optimal donor(s) as output of the trained machine learning model. In some examples, when there is more than one optimal donor identified and recommended, the optimal donors may be ranked. In some examples, the donors may be ranked based on a mathematical distance between the respective recipient embeddings and the patient embedding in the embedding space. For example, a donor of the most similar recipient is ranked highest. Additionally and/or alternatively, the donors may be ranked on additional metadata associated with the donor-recipient pair profiles (e.g., stored in the database). The additional metadata may include qualitative data related to an outcome of the recipient of the donor-recipient pair. For example, a donor of a donor-recipient pair whose recipient had a quicker recovery, a longest survival rate, and/or required the least amount of immunosuppressant to prevent rejection, may be ranked highest. The additional metadata may also include qualitative data related to a health of the donor of the donor-recipient pair. For example, a donor having a better health provided based on exercise performance, overall fitness, lung capacity, age, and/or other similar health factors may be ranked highest.

At step 460, the system may save the recommendation to a digital storage 109 (e.g., to a medical record associated with the patient). In some examples, the recommendation may be transmitted to an electronic health care record system to be included (e.g., stored within) a medical record associated with the patient. This may include transmitting the prediction by electronic network 120 to either the hospital servers 122, the research lab server 124, laboratory information systems 125, the physician servers 121, or clinical trial servers 123. In further examples, the prediction may be provided as input to other systems such as transplant databases.

In some examples (e.g., dependent on a type of the transplant), in addition to recommending an optimal donor, the system may also be trained and implemented to recommend a delivery type for the transplant. For example, for an FMT, the fecal microbiota may be transplanted in a pill form orally consumed by the patient or in a liquid form inserted rectally into the gastrointestinal tract. In such examples, the training data used to train the machine learning model may include data associated with the delivery type used for each donor-recipient pair.

The dietary and lifestyle prediction module 206, described in FIGS. 5A and 5B below, may be applied to a patient in response to determining a recommendation from the donor recipient inference module 204. In another example, the dietary and lifestyle prediction module 206 may be applied as a separate system. Other techniques described herein used in conjunction or separately with the above-described identification of optimal transplant donor-recipient matches may include application of AI technology, machine learning, and/or image processing tools to provide lifestyle recommendations (e.g., diet and exercise recommendations) to improve a patient's quality of life and/or extend their lifespan.

Figure 5A:
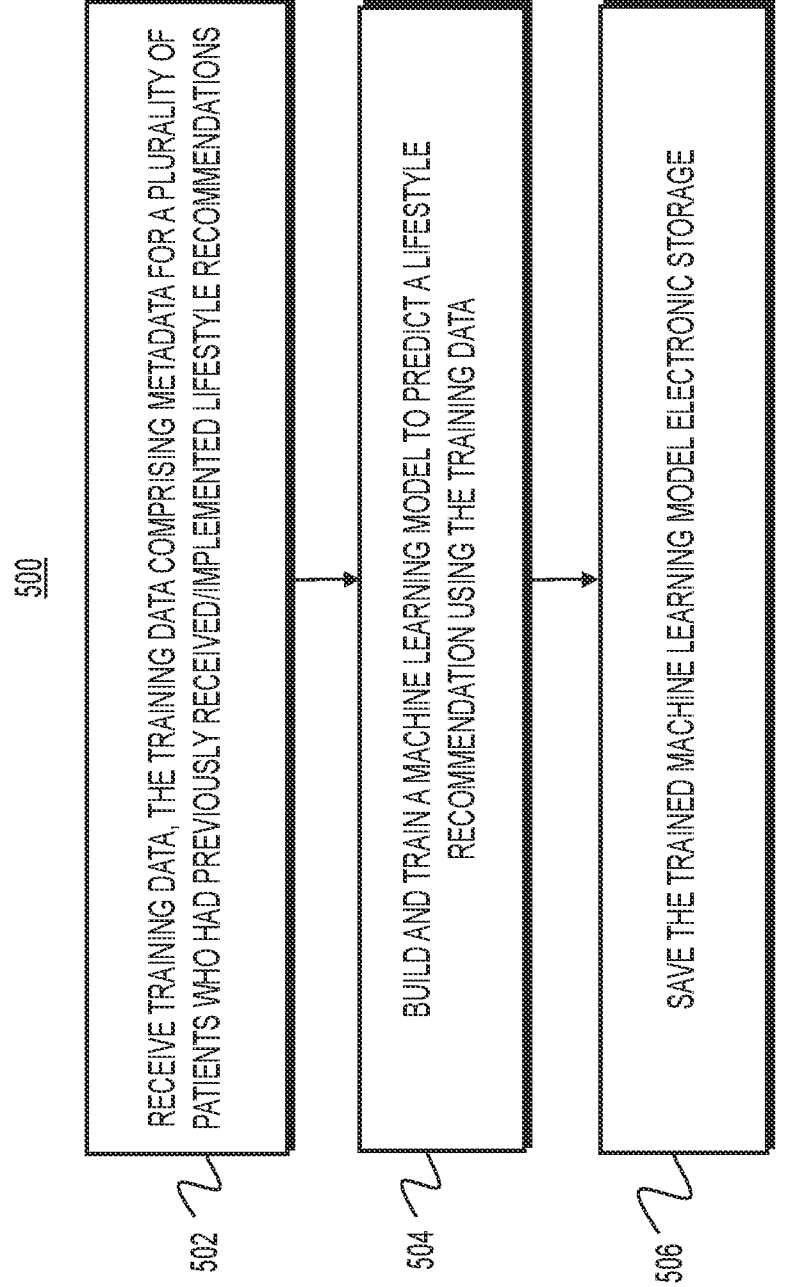
FIG. 5A is a flowchart illustrating an example method of training a dietary, lifestyle, and lifespan recommendation module according to an exemplary embodiment of the present disclosure.

FIG. 5A is a flowchart illustrating an example method 500 of training a dietary and lifestyle prediction module 206 according to an exemplary embodiment of the present disclosure. The method 500 of FIG. 5A depicts steps that may be performed by, for example, the dietary and lifestyle tool 144 as described above. Alternatively, the method 500 may be performed by an external system.

According to one example aspect for training a machine learning model to predict lifestyle recommendations, method 500 may be performed.

At step 502, the system may receive training data into a digital storage device 109 (e.g., hard drive, network drive, cloud storage, RAM, etc.). The training data may include metadata for a plurality of patients who had previously received/implemented lifestyle recommendations. The metadata may include BMI, percentage of body fat, age, gender, ethnicity, pathology WSI, radiology images, microbial composition, genomics (e.g., longevity regulating pathway alterations), transcriptomics, and/or metabolomics. The metadata may also include an initial set of lifestyle attributes associated with the patient, such as a diet and/or exercise of the patient prior to the patient receiving/implementing the lifestyle recommendations. In some examples, the patients include recipients of a particular type of transplant (e.g., FMT recipients, heart transplant recipients, kidney transplant recipients, etc.) and/or recipients at a high risk for a particular type of disease (e.g., heart disease, cancer, etc.). In some examples, the training data may also include labels associated with specific lifestyle attributes associated with diet, exercise, etc. that improved (and/or alternatively did not improve) a quality of life of the patient.

At step 504, the system may build and train a machine learning model to predict a lifestyle recommendation using the training data from step 502. As part of the training process, for the metadata of a given patient, the machine learning model may learn to characterize the metadata into embeddings, evaluate the embeddings for a signal or a cluster of signals, and predict a lifestyle recommendation based on the signal or cluster of signals. In some examples, the characterization of the patient's metadata into embeddings may include at least characterizing morphology of available tissue such as fatty tissue, muscle tissue, stromal tissue, necrotic tissue, cancerous tissue, inflamed tissue etc. (e.g., from the pathology WSI and/or radiology images of the training data). In some examples, the machine learning model is trained using a semi-supervised, multiple instance learning approach. In other examples, other machine learning approaches (e.g., supervised, unsupervised, semi-supervised) may be utilized. In some examples, the system may include a first tool for determining embeddings and a second tool for analyzing the embeddings and outputting a recommendation.

At step 506, the system may save the trained machine learning model to electronic storage (e.g., electronic storage 109).

According to one example aspect, to implement a trained learning model for predicting a lifestyle recommendation for a target patient, method 550 may be performed.

FIG. 5B is a flowchart illustrating an exemplary method of performing a dietary and lifestyle prediction according to an exemplary embodiment of the present disclosure. The exemplary method 550 (e.g., steps 552-560) of FIG. 5B depicts steps that may be performed by, for example, by the dietary and lifestyle tool 144. These steps may be performed automatically or in response to a request from a user (e.g., physician, pathologist, etc.). These steps may describe an exemplary method of how to use the trained system described in FIG. 5A. Alternatively, the method described in flowchart 550 may be performed by any computer process system capable of receiving image inputs such as device 900 and capable of including or importing the neural network described in FIG. 5A. The machine learning system of method 550 may be implemented to determine dietary and/or lifestyle suggestions for a target patient. The target patient may, for example, be in need of a transplant.

At step 552, the system may receive the trained machine learning model from FIG. 5A.

At step 554, the system may receive metadata for a target patient, such as BMI, percentage of body fat, age, gender, ethnicity, pathology WSI, radiology images, microbial composition, genomics (e.g., longevity regulating pathway alterations), transcriptomics, and/or metabolomics. The metadata may also include a current state associated with the target patient's lifestyle (e.g., current diet, current exercise, etc.).

At step 556, the system may provide the metadata as input to the trained machine learning model received at step 552. The trained machine learning model may characterize morphology of available tissue such as fatty tissue, muscle tissue, stromal tissue, necrotic tissue, cancerous tissue, inflamed tissue etc. (e.g., from the pathology WSI and/or radiology images) into embeddings. Additionally, the remaining metadata may be characterized into embeddings. These embeddings may be evaluated by the trained machine learning model for a signal or a cluster of signals. For example, this may be performed by techniques such as k-means clustering. Based on the signal or cluster of signals identified, the trained machine learning model may provide, as output, a lifestyle recommendation associated with one or more diet and/or exercise regimens that could lead to improvements in the patient's quality of life (e.g., increase lifespan).

At step 558, the system may receive the lifestyle recommendation output by the trained machine learning model. Life system recommendations may include: particular exercise regimes, a dietary output (e.g., foods to avoid and include in one's diet, food portions to eat, etc.), sleep schedules, suggested physical fitness objectives/goals, etc. The recommendation output may, for example, determine that the muscle tissue on the digital medical images looks insufficient and then output a recommendation to increase/supplement protein intake (e.g., a dietary output).

At step 560, the system may save the lifestyle recommendation to digital storage 109 (e.g., store in an electronic medical record of the patient).

In one example, when a specific fatty tissue morphology in a specific organ of a patient is identified, the lifestyle recommendation may include a specific diet and/or exercise regimen to reduce the amount of fatty tissue. Implementation of this recommendation by the patient may lead to weight loss and/or a reduction in the progression or development of future diseases such as cancer. In another example, for an FMT recipient, a lifestyle recommendation may be provided to specifically maintain the health of the patients' microbiome post-transplant.

Similar techniques may also be applied to analyze the microbiomes of donors over time in terms of diet, lifestyle, exercise, etc. to determine which lifestyle types maintain optimal bioflora. In some scenarios, these optimal lifestyle types may be used to further rank donors determined to be optimal for a patient in need of a transplant by the above-described systems and methods for identifying optimal transplant donor-recipient matches. For example, a donor having a lifestyle type determined to maintain optimal bioflora may be selected over another donor having a less optimal lifestyle type.

Other techniques described herein used in conjunction or separately with the above-described identification of optimal transplant donor-recipient matches and/or providing of lifestyle recommendations may include automatically notifying donor collection entities, e.g., hospitals, of a need for donors with a given profile. This may be performed by, for example, the tissue viewing platform 100. As part of the automatic notification system, a patient at a hospital who meets the given profile, among other requirements for transplant, could be flagged to prompt a medical professional to discuss with the patient if they would be willing to be a donor for the relevant application, e.g., liver transplant, fecal transplant, kidney transplant, etc. Additionally or alternatively, candidate donors for critical organ removal (e.g., brain dead or very recently deceased individuals) meeting the given profile may be matched.

For example, when an optimal donor is identified for a patient in need of a transplant using the above-described systems and methods for identifying optimal transplant donor-recipient matches, an additional evaluation may be performed to determine whether to trigger automatic notification. As one example, if the output of the system for identifying optimal transplant donor-recipient matches is a list of optimal donors, but each of those donors have already donated and/or are not applicable for a second donation, the automatic notification may be triggered. The notification may include metadata of the patient in need, an indication of the donor profile needed that matches the recipient, and/or a request for the donor collection entities to start collecting donors that have a similar profile.

In other examples, a threshold for triggering the automatic notification may be based on a list of donors having a given profile being less than N. For example, the system may periodically check a database listing donors and their associated donor profiles for a given type of transplant. Based on the periodic checks, if the number of donors having a given profile are below a threshold number or, in the case of FMTs, if it is determined that there are limited (or no) samples remaining in a stool bank for the optimal donor and/or donors having a similar profile to the optimal donor, the automatic notification may be triggered.

In further examples, patterns or trends in transplant needs may be learned overtime, and the automatic notification may be triggered proactively to ensure that there are sufficient donors and/or donor samples to fulfill the needs. Example patterns or trends learned may include an increase at a healthcare facility for transplant requests from recipients or less transplant donors volunteering, which may prompt the healthcare facility to proactively increase donor outreach and awareness programs. Other example patterns or trends learned may include population dietary trends, where a trend of popularity of a diet incorporating a particular food product that may lead to an increase in transplant need may be measured in order to predict future number of donors to fulfill transplant needs. Further example patterns or trends learned may be associated with publications and/or new transplant method trials or approvals. A separate machine learning model may be trained to learn the patterns or trends over time to predict future demand. This may be performed by, for example, slide analysis tool 101. Alternatively, this may be performed by an external system capable of receiving image inputs such as device 900. For example, inputs to the machine learning model may include data collected from a plurality of resources such as: a number of recipients and/or donors or a donor-recipient ratio from healthcare facilities; sales data on foods and beverages from food and beverage retailers and/or social media popularity data associated with foods and beverages; population-based feedback and/or publication and regulatory announcement from entities such as the National Wastewater Surveillance System (e.g., measurements of microbes, metabolites or viruses in waste water) and the Food and Drug Administration; and/or drug sales data (e.g., indicating a correlation between a particular medication use and a transplant increase).

Figure 6:
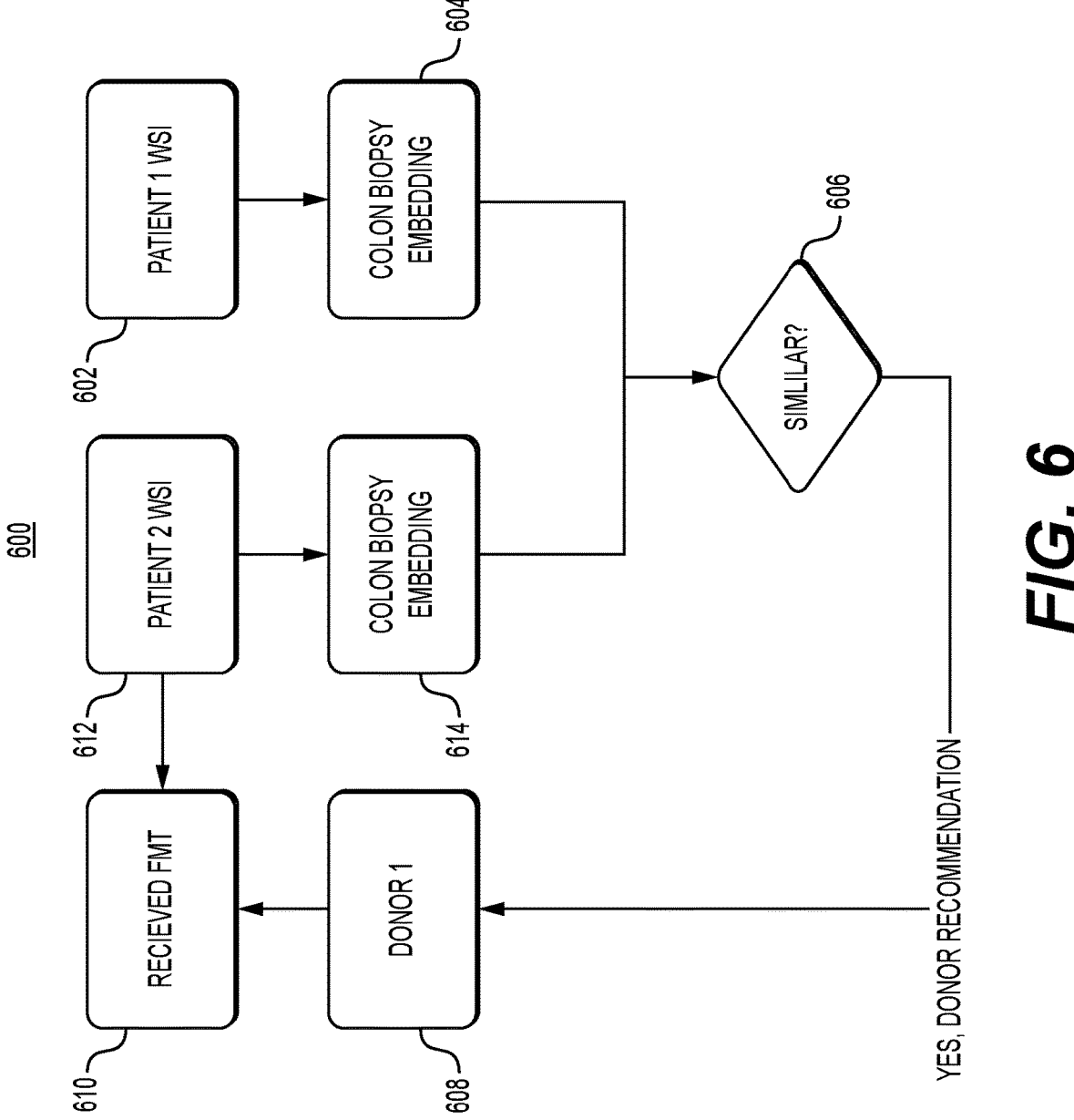
FIG. 6 illustrates an exemplary process for determining a FMT donor recipient, according to techniques presented herein.

FIG. 6 illustrates an exemplary process 600 for determining a FMT donor recipient, according to techniques presented herein. One example use case or application of one or more of the above-described systems includes a scenario where a patient (e.g., patient 1) needs an FMT to treat a gastrointestinal disease, such as *Clostridium difficile* colitis. The patient may undergo a colon polyp biopsy and/or colon resection. A whole slide image (WSI) 602 of the colon tissue biopsied and/or resected may be created. At least the WSI 602 may be provided as input to the above-described system for identifying an optimal transplant donor-recipient match. For example, one or more WSI 602 (patient 1 WSI) may be provided as input to a trained machine learning model (e.g., the donor recipient inference tool 141) and a colon biopsy embedding 604 may be determined. The colon biopsy embedding 604 determined from the WSI 602 may be based on an analysis of the morphology and structure of the tissue to indicate attributes thereof (and optionally other patient 1 metadata provided as input to the trained machine learning model). The trained machine learning model may be implemented by, for example, the donor recipient inference tool 141. The trained machine learning model may utilize a similarity function to identify a subset of recipients (e.g., from recipients of donor-recipient pair profiles stored in a database and used to train the model) that have previously undergone an FMT from donors and are similar to patient 1. For example, colon biopsy embeddings may have been learned for the recipients in the embedding space based on colon biopsy WSIs for the recipients as part of the training process, and a similarity function may be performed to indicate how similar a given recipient embedding is to the embedding for patient 1 based on a distance between the embeddings in the embedding space. Patient 2 may be an identified recipient donor. Patient 2 may have previously performed a colon polyp biopsy and/or colon resection and determined a WSI 612. As illustrated, a colon biopsy embedding 614 (determined by the trained machine learning model) for patient 2 (e.g., based on the patient 2's WSI 612) may be determined to be similar 606 (e.g., within a threshold distance in the embedding space) to the colon biopsy embedding for patient 1. This may be performed by the trained machine learning model. In some examples, one or more other recipients may be identified in addition to patient 2 within the subset as being similar to patient 1. From the subset of recipients identified, those recipients who had a successful transplant outcome may be further identified (e.g., by referencing the database storing the donor-recipient pair profiles), and donors for those patients may be provided as recommended optimal donor(s) for the target recipient. This may include for example donor 1 608. For example, at least patient 2 identified being as similar patient 1 may have had a successful outcome, and thus the donor of patient 1's FMT is identified from the information within the database and is provided in the recommendation. Information regarding patient 2's donor 1 608 and the received fecal matter transplant 610 may be recorded and saved.

When more than one optimal donor is identified, the donors may be ranked based a mathematical distance between the recipient embedding of the recipient from the donor-recipient pair (e.g., patient 2) and the patient embedding of the (e.g., patient 1) in the embedding space. For example, a donor of the most similar patient is ranked highest (e.g., this may be referred to as donor 1 608). Additionally and/or alternatively, the donors may be ranked on additional metadata associated with donor-recipient pair (e.g., stored in the database). The additional metadata may include qualitative data related to an outcome of the patient of the donor-recipient pair. For example, a donor of a donor-recipient pair whose recipient had a quicker recovery, had a longest survival rate, and/or patient required the least amount of immunosuppressant to prevent rejection, among other similar examples, may be ranked highest.

Further, for FMTs, donor collection entities, e.g., hospitals, may include a stool bank that includes a plurality of stool samples from each donor. In some examples, the stool of the donors may undergo microbiome sequencing to identify the microbial composition of the donor' gastrointestinal tracts. Once an optimal donor, e.g., donor 1, is identified/recommended, a sample of the donor's stool (e.g., FMT 610) may be retrieved from the bank for use in the FMT procedure. In scenarios where no stool samples for the optimal donor remain, a substitute donor may be determined by identifying a stool sample having similar microbiome sequencing to the stool sample of the optimal donor. In some examples, these types of scenarios may also trigger an automatic notification to the donor collection entities to prompt collection of more stool samples, if available, from the optimal donor (e.g., donor 1 608) and/or from other donors having a similar profile to the optimal donor.

Figure 7:
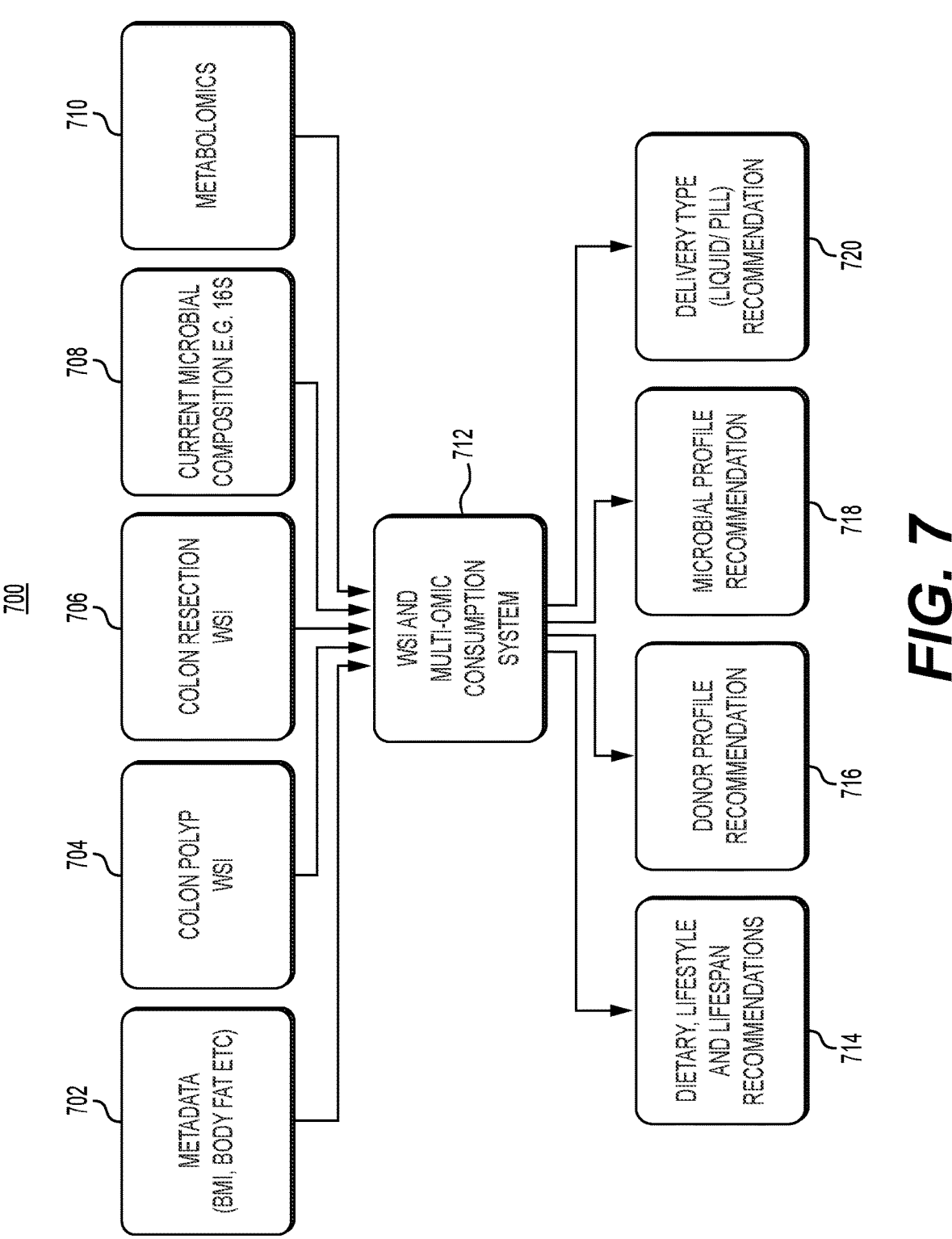
FIG. 7 illustrates an exemplary process for to determining a dietary, lifestyle and lifespan recommendations, and/or a delivery type recommendation, according to techniques presented herein.

FIG. 7 illustrates an exemplary process 700 for to determining a dietary, lifestyle and lifespan recommendations, and/or a delivery type recommendation, according to techniques presented herein. FIG. 7 may include receiving one or more trained machine learning systems 712 (e.g., the donor recipient inference tool 141 and the dietary and lifestyle tool 144) being determined and/or received. The trained machine learning systems 712 may collectively be referred to as a WSI and multi-omic consumption system. The one or more trained machine learning systems 712 may then, for example through network 120, receive information related to a patient. The patient may be in need of a donor transplant. The one or more trained machine learning systems 712 may first receive a colon polyp WSI 704, and/or a colon resection WSI 706 for a patient. The one or more trained machine learning systems may receive additional biopsy WSIs.

In addition to the colon polyp WSI 704 and/or resected colon WSIs 706 of the patient (patient 1) discussed above, the one or more trained machine learning systems 712 can consume additional metadata 702 of the patient such as body fat composition, BMI, etc. Furthermore, the one or more trained machine learning systems 712 may also take in current microbial composition (e.g., 16S) 708 and metabolomics 710. The one or more trained machine learning systems 712 may then determine embeddings for the received information. In one example, the system may determine a first set of embeddings related to a donor profile and a second set of embeddings related to the patient's diet and lifestyle.

Based on the first set of embeddings, the one or more trained machine learning systems 712 may determine a donor profile recommendation 716. Based on the second set of embeddings, the one or more trained machine learning systems 712 may determine a dietary, lifestyle, and lifespan recommendations 714.

Resultantly, in addition to predicting an optimal donor for the patient (e.g., a donor profile recommendation 716) and providing dietary lifestyle and lifespan recommendations 714, the one or more trained machine learning systems 712 may predict and recommend beneficial microbial profiles 718, and/or a delivery type recommendation 720 (pill vs. liquid) in relation to the microbial profile recommendation 720.

FIG. 8 illustrates an exemplary flowchart 800 for processing images to determine a donor recipient prediction, according to techniques presented herein.

At step 802, a digital medical image of the patient may be received, wherein the patient is in need of a transplant.

At step 804, a trained machine learning system may be determined.

At step 806, the digital medical image may be provided into the trained machine learning system, the trained machine learning system determining a patient embedding.

At step 808, using the patient embedding, a subset of donor recipients may be determined.

At step 810, based on the subset of donor recipients a recommendation of optimal donors may be determined.

Figure 9:
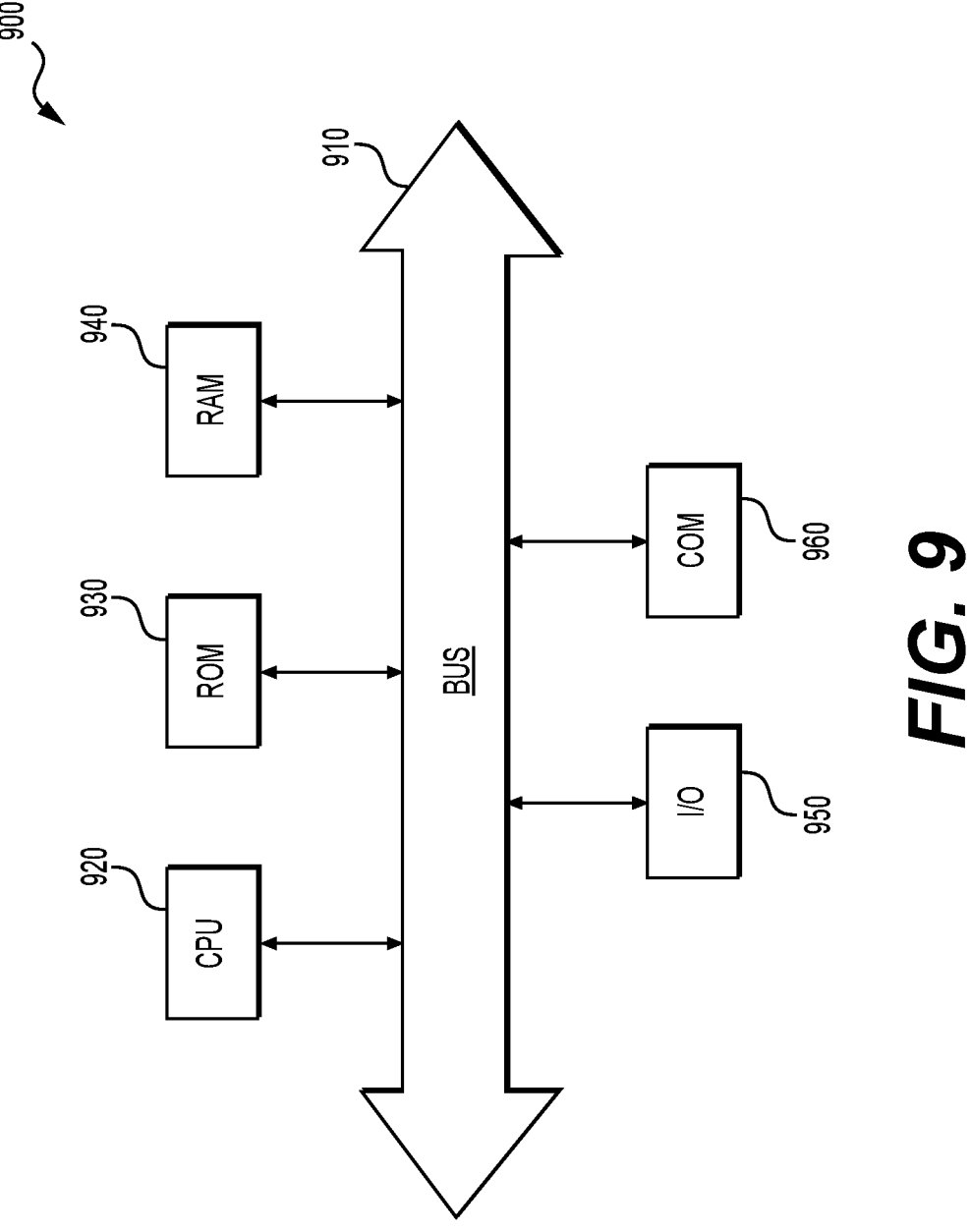
FIG. 9 depicts an example of a computing device that may execute techniques presented herein, according to one or more embodiments.

FIG. 9 depicts an example of a computing device that may execute techniques presented herein, according to one or more embodiments.

As shown in FIG. 9, device 900 may include a central processing unit (CPU) 920. CPU 920 may be any type of processor device including, for example, any type of special purpose or a general-purpose microprocessor device. As will be appreciated by persons skilled in the relevant art, CPU 920 also may be a single processor in a multi-core/multi-processor system, such system operating alone, or in a cluster of computing devices operating in a cluster or server farm. CPU 920 may be connected to a data communication infrastructure 910, for example a bus, message queue, network, or multi-core message-passing scheme.

Device 900 may also include a main memory 940, for example, random access memory (RAM), and may include a secondary memory 930. Secondary memory 930, for example a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 930 may include similar means for allowing computer programs or other instructions to be loaded into device 900. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 900.

Device 900 also may include a communications interface ("COM") 960. Communications interface 960 allows software and data to be transferred between device 900 and external devices. Communications interface 960 may include a modem, a network interface (such as an Ethernet card), a communications port, a PCMCIA slot and card, or the like. Software and data transferred via communications interface 960 may be in the form of signals, which may be electronic, electromagnetic, optical or other signals capable of being received by communications interface 960. These signals may be provided to communications interface 960 via a communications path of device 900, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 900 may also include input and output ports 950 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

While the above-discussed use case describes the application of the system for an FMT, techniques presented herein may be applied in a variety of different transplant applications.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

23

What is claimed is:

1. A computer-implemented method for processing electronic medical images to predict one or more donors for a subject, comprising:

receiving a digital medical image of the subject, wherein the subject is in need of a transplant;

determining a trained machine learning system;

providing the digital medical image into the trained machine learning system, the trained machine learning system determining a subject embedding;

determining, using the subject embedding, a subset of donors;

determining based on the subset of donors a recommendation of optimal donors; and determining a second trained machine learning system, the second trained machine learning system being capable of determining a dietary, sleep, or exercise suggestion, wherein the second trained machine learning system receives as input the digital medical image of the subject, determines a lifestyle embedding, and determines, based on the lifestyle embedding, a dietary, sleep, or exercise suggestion for the subject.

2. The method of claim 1, wherein the transplant is a fecal matter transplant.

3. The method of claim 1, wherein the transplant is a liver transplant.

4. The method of claim 1, wherein a salient region detection module is applied to determine a saliency of each region within the received digital medical image, and non-salient image regions are excluded from processing by the trained machine learning system.

5. The method of claim 1 further including:

receiving metadata corresponding to the subject, the metadata comprising: clinical data, genetic information, microbial composition, and/or life history data; and providing the metadata into the trained machine learning system.

6. The method of claim 1, further including:

notifying, with a notification, donor collection entities of a need for donors with a given profile.

7. The method of claim 6, wherein the notification may include metadata of the subject in need, an indication of the donor profile needed that matches the recipient, and/or a request for the donor collection entities to start collecting donors that have a similar profile.

8. A system for processing electronic medical images to predict one or more donors for a subject, the system comprising:

at least one memory storing instructions; and at least one processor configured to execute the instructions to perform operations comprising:

receiving a digital medical image of the subject, wherein the subject is in need of a transplant;

determining a trained machine learning system;

providing the digital medical image into the trained machine learning system, the trained machine learning system determining a subject embedding;

determining, using the subject embedding, a subset of donors;

determining based on the subset of donors a recommendation of optimal donors; and determining a second trained machine learning system, the second trained machine learning system being capable of determining a dietary, sleep, or exercise suggestion, wherein the second trained machine learning system receives as input the digital medical image of the subject, determines a lifestyle embedding, and determines, based on the lifestyle embedding, a dietary, sleep, or exercise suggestion for the subject.

9. The system of claim 8, wherein the transplant is a fecal matter transplant.

10. The system of claim 8, wherein the transplant is a liver transplant.

11. The system of claim 8, wherein a salient region detection module is applied to determine a saliency of each region within the received digital medical image, and non-salient image regions are excluded from processing by the trained machine learning system.

12. The system of claim 8 further including:

receiving metadata corresponding to the subject, the metadata comprising: clinical data, genetic information, microbial composition, and/or life history data; and providing the metadata into the trained machine learning system.

13. The system of claim 8 further including:

notifying, with a notification, donor collection entities of a need for donors with a given profile.

14. The system of claim 13, wherein the notification may include metadata of the subject in need, an indication of the donor profile needed that matches the recipient, and/or a request for the donor collection entities to start collecting donors that have a similar profile.

15. A non-transitory computer-readable medium storing instructions that, when executed by a processor, perform operations processing electronic medical images to predict one or more donors for a subject, the operations comprising:

receiving a digital medical image of the subject, wherein the subject is in need of a transplant;

determining a trained machine learning system;

providing the digital medical image into the trained machine learning system, the trained machine learning system determining a subject embedding;

determining, using the subject embedding, a subset of donors recipients; and determining based on the subset of donors a recommendation of optimal donors; and determining a second trained machine learning system, the second trained machine learning system being capable of determining a dietary, sleep, or exercise suggestion, wherein the second trained machine learning system receives as input the digital medical image of the subject, determines a lifestyle embedding, and determines, based on the lifestyle embedding, a dietary, sleep, or exercise suggestion for the subject.

16. The non-transitory computer-readable medium of claim 15, further including:

receiving metadata corresponding to the subject, the metadata comprising: clinical data, genetic information, microbial composition, and/or life history data; and providing the metadata into the trained machine learning system.

17. The non-transitory computer-readable medium of claim 15, further including:

notifying, with a notification, donor collection entities of a need for donors with a given profile, wherein the notification may include metadata of the subject in need, an indication of the donor profile needed that matches the recipient, and/or a request for the donor collection entities to start collecting donors that have a similar profile.

\* \* \* \* \*